United States Patent
Carman

(10) Patent No.: US 6,750,376 B1
(45) Date of Patent: Jun. 15, 2004

(54) METHODS FOR PRODUCING APOMICTIC PLANTS

(75) Inventor: John G. Carman, Smithfield, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 09/576,623

(22) Filed: May 23, 2000

Related U.S. Application Data

(63) Continuation of application No. 09/018,875, filed on Feb. 5, 1998, now abandoned.
(60) Provisional application No. 60/037,211, filed on Feb. 5, 1997.

(51) Int. Cl.$^7$ ................................................. A01H 1/02
(52) U.S. Cl. ........................................ 800/260; 800/269
(58) Field of Search ................................. 800/260, 269, 800/266, 271, 273, 295, 298; 435/410

(56) References Cited

U.S. PATENT DOCUMENTS 5,710,367 A     1/1998   Kindiger et al. ............ 800/200

OTHER PUBLICATIONS

Bashaw et al. 1987. Chapter 3: Apomictic grasses. Pp. 40–82, In: Principles of Cultivar Development, vol. 2: Crop Species. MacMilan Publishing Co., NY.*
Bates et al. 1974. Wide Crosses. In: Proceedings of World-wide maize improvement in the 70's and the role of CIMMT, Apr. 22–26 El Batan, Mexico. 7 pp. CIMMT.*
Carman et al. 1997. Asynchronous expression of duplicate genes in angiosperms may caus apomixis, bispory, tetraspory, an dpolyembryony. Biol. J. Linn. Soc. 61:51–94.*
Dung et al. 1998. Dissection of a major QTL for photoperiod sensitivity in rice: its association with a gene expresses in an age–dependent manner. Theor Appl. Genet. 97:714–720.*
Eshed et al. 1996. Less–than–epistatic interactions of quantiative trait loci in tomato. Genetics 143:1807–1817.*
Garcia et al. 2000. Genetic variation in the progeny of maize/Tripsacum hybrids. Maize Genet. Coop. Newsletter 74:40–41.*
Hanna et al. 1987. Apomixis: Its identification and use in plant breeding. Crop Sci. 27 :1136–1139.*
Holm et al. 1996. Sexuality and no apomixis found in crossing experiments withdiploid *Potentilla argentea*. Hereditas 125:77–82.*
Hovin et al. 1976. Effects of geographic origin and seed production environments on apomixis in Kentucky bluegrass. Crop Sci. 16 :635–638.*
Kenny et al. 1996. A test of the general–purpose genotype hypothesis in sexual and asexual Erigeron species. The American Midland Naturalist 136(1):1–13.*
Koltunow et al. 1995. Apomixis: Molecular strategies for the generation fof genetically identical seeds without fertilization. Plant Physiol. 108:1345–1352.*

Kraft et al. 2000. Linkage disequilibrium and fingerprinting in sugarbeet. Theor. Appl. Genet. 101:323–326.*
Purnhauser et al. 1993. A method fro crossing non–synchronously flowering parents in wheat, using cold storage of the female parent. Cereal Res. Comm. 21 (2–3):175–179.*
Saran et al. 1976. Environmental control of reproduction in *Dichanthium intermedium*. J. Cytol. Genet. 11:22–28.*
That et al. 1987, The development of new rice hybrids. Rice Int. Commission Newsletter 42:28–34.*
de Wet et al. 1970. Stable triploid hybrids among Zea–Tripsacum–Zea backcross populations. Caryologia 23 : 183–87.*
Johri et al., Comparative Embryology of Angiosperms, Vol 1: pp. 1–4, 29–41, 84–94, 1992.
Asker and Jerling, Apomixis in Plants, pp. 49–80, 1992.
Carman et al., Comparative histology of cell walls during meiotic and apomeiotic megasporogenesis in two australasian Elymus L. species. Crop Sci. 31:1527–1531. 1991.
Peel et al. Megasporocyte callose in apomictic buffelgrass, Kentucky bluegrass, *Pennisetum squamulatum* Fresen, Tripsacum L. and weeping lovegrass. Crop Sci. 37:724–732. 1997.
Naumova and Willemse, Ultrastructural characterization of apospory in *Panicum maximum*, Sex Plant Repord 8: 197–204. 1995.
Naumova et al. Apomixis in plants: structural and functional aspects of diplospory in *Poa nemoralis* and *P. palustris*, Protoplasma 208:186–195, 1995.
Sherwood. Genetic analysis of apomixis, in Savidan et al ed., The Flowering of Apomixis: From Mechanisms to Genetic Engineering, D.F.: CIMMYT, IRD, EC DG VI, FAIR 2001.
Gustafsson Å. Apomixis in higher plants. III. Biotype and species formation. Lunds Universitets Årsskrift 43: 181–370. 1947.
Mogie M. The evolution of asexual reproduction in plants. London: Chapman and Hall. 1992.
Carman JG. Asynchronous expression of duplicate genes in angiosperms may cause apomixis, bispory, tetraspory, and polyembryony. Biol J. Linnean Soc 61: 51–94. 1997.

(List continued on next page.)

*Primary Examiner*—Amy J. Nelson
*Assistant Examiner*—Anne Kubelik
(74) *Attorney, Agent, or Firm*—Winston & Strawn LLP

(57) ABSTRACT

Methods are provided for producing apomictic plants from sexual plants divergent with respect to responses to different photoperiods and schedules of megaspore and gametophyte development. A preferred system is to identify divergent plants from within a species or closely related group of species, accentuate the divergence by breeding, and produce artificial amphiploids that contain genomes from the apposing divergent plants. Apomixis results from the asynchronous expression of female developmental programs induced by crossing the reproductively divergent plants. The procedures for manipulating the expression of apomixis described herein permit the development of true-breeding hybrids of various cultivated crops.

17 Claims, 4 Drawing Sheets

OTHER PUBLICATIONS

Sherwood et al. Inheritance of apospory in buffelgrass, Crop Sci 34:1490–1494, 1994.

Leblanc et al. Detection of the apomictic mode of reproduction in maize–Tripsacum hybrids using maize RFLP markers, Theor Appl Genet 90: 1198–1203, 1995.

Carman JG, The evolution of gametophytic apomixis, In Batygina (ed) Embryology of Flowering Plants, vol. 3, The Systems of Reproduction, Russian Acad. Sci, St. Petersburg. 230–236. 2000.

Grimanelli et al, Mapping diplosporous apomixis in tetraploid Tripsacum: one gene or several genes, Heredity 80:33–39. 1998.

Ozias–Akins et al. Tight clustering and hemizygosity of apomixis–linked molecular markers in *Pennisetum squamulatum* implies genetic control of apospory by a divergent locus that may have no allelic form in sexual genotypes, Proc Natl Acad Sci 95:5127–5132.

Ramula et al. Apomixis for crop improvement, Protoplasma 208: 196–205 (see Abstract and Conclusions). 1999.

Jefferson and Bicknell, The potential impacts of apomixis: a molecular genetics approach, in *The Impact of Plant Molecular Genetics*, Birkhauser, Boston, pp. 88–89, 94, 98). 1996.

Kultunow et al. Apomixis: molecular strategies for the generation of genetically identical seeds without fertilization, Plant Physiol 108: 1345–1352, 1995.

Asker and Jerling, Apomixis in Plants, p. 114, 1992.

Asker and Jerling, Apomixis in Plants, p. 81–107, 241–283. 1982.

Bashaw, Apomixis and its Application in Crop Improvement, in Fehr (ed) *Hybridization of Crop Plants*, pp. 45–63. 1980.

Baum et al. Wide Crosses in Cereals. Annu. Rev. Plant Physiol. Plant Mol. Biol., 43:117–43, 1992.

Ozias–Akins, Characterization of the Genomic Region Associated with the Transmission of Apomixis in Pennisetum and Cenchrus, presented at Plant & Animal Genome XI, The International Conference on the Status of Plant & Animal Genome Research: Town & Country Hotel, San Diego, California, Jan. 11–15, 2003.

Carman, Evolution of Apomixis in Antennaria (Asteraceae): A Model Involving Hybrid Origins and Karyotypic Stabilization, presented at Plant & Animal Genome XI, The International Conference on the Status of Plant & Animal Genome Research. Town & Country Hotel, San Diego, California, Jan. 11–15, 2003.

Sharbel et al. Genome–Wide Genetic Variability and DNA Sequence Divergence along an Aneuploid Chromosome Associated with Apomixis in the *Arabis holboellii* Complex, presented at Plant & Animal Genome XI, The International Conference on the Status of Plant & Animal Genome Research. Town & Country Hotel, San Diego, California. Jan. 11–15, 2003.

Barcaccia et al. Comparison between isozyme and RAPD analyses to screen aberrant plants in *Poa pratensis* L. progenies, in Apomixis Newsletter, 7:29–30. 1994.

Evans et al., Environmental Control of Reproduction in *Themeda australis*, Aust. J. Bot., 17:375–89. 1969.

Hussey et al. Influence of photoperiod on the frequency of sexual embryo sacs in facultative apomietic buffelgrass, Euphytica 54:141–145. 1991.

Liu et al. Hybrids and backcross progenies between wheat (*Triticum aestivum* L.) And apomictic Australian wheatgrass [*Elymus rectisetus* (Nees in Lehm.) A. Löve & Connor]: karyotypic and genomic analyses, Theor Appl Genet, 89:599–605. 1994.

Mogie, The Evolution of Asexual Reproduction in Plants, 139–196. 1992.

Poehlman, Breeding Field Crops, $3^{rd}$ Ed., pp. 164–165, 332–339. 1987.

Salisbury et al. Plant Physiology, $4^{th}$ Ed., pp. 504–514. 1992.

Torabinejad et al. Morphology and genome analyses of interspecific hybrids of *Elymus scabrus*, Genome, 29:150–155, 1987.

Zenkteler. In Vitro Fertilization and Wide Hybridization in Higher Plants, Critical Reviews in Plant Sciences, 9: 267–279. 1990.

Battaglia E., *The Evolution of the Female Gametophyte of Angiosperms: an Interpretive Key*, Annali di Botanica 47:7–144(1989).

Bayer, R. J., *Evolution of Polyploid Agamic Complexes with Examples from Antennaria (Asteraceae)*, Opera Botanica 132:53–65 (1996).

Bell, P.R., *Apospory and Apogamy: Implications for Understanding the Plant Life Cycle*, International Journal of Plant Sciences 153: S123–S136 (1992).

Bennett, S.T. et al., *Spatial Separation of Ancestral Genomes in the Wild Grass Milium montianum Parl.*, Annals of Botany 70: 111–118 (1992).

von Bothmer, R. et al., *Complex Interspecific Hybridization in Barley (Hordium vulgare L and the Possible Occurrence of Apomixis*, Theoretical and Applied Genetics 76:681–690 (1988).

Carman, John G., *Asynchronous Expression of Duplicate Genes in Agniosperms May Cause Apomixis, Bisporty, Tetrasporty, and Polyembryony*, Biological Journal of the Linnean Society 61, 51–94 (1997).

Carman, J. G., *Gametophytic Angiosperm Apomicts and the Occurrence of Polyspory and Polyembryony Among Their Relatives*, Apomixis Newsletter 8: 39–53 (1995).

Carman, J.G., *Phylogeny of Apomictic, Polysporic and Polyembryonic Angiosperms: Evolutionary and Regulatory Implications*, Abstract of a paper presented at the international conference, Harnessing, Apomi Sep. 25–27, College Station, Texas (1995).

Carman, J. G. et al., *Comparative Histology of Cell Walls During Meiotic and Apomeiotic Megasporoge in Two Hexaploid Australian Elymus species*, Crop Science 31: 1527–1532 (1991).

Carman, J. G. et al., *Asporous Apomixis in Schizachyrium (Poaceae:Andropogoneae)*, Crop Science 2 1252–1255 (1982).

Crane, C. F. et al., *Mechanisms of Apomixis in Elymus rectisetus from Eastern Australia and New Zeala* American Journal of Botany 74: 477–496.

DeWet, J.M.J. et al., *Gametophytic Apomixis and Evolution in Plants*, Taxon 23: 689–697 (1974).

Ellerstrom S., *Apomictic Progeny from Raphanobrassica*, Hereditas 99: 315 (1983).

Ellerstrom S. et al., *Sterility and Apomictic Embryo Sac Formation in Raphanobrassica*, Hereditas 87: 10 (1977).

Evans, L. T. et al., *Environmental Control of Reproduction in Themeda australis* Australian Journal of Botany 17: 375–389 (1969).

Hussey, M.A. et al., *Influence of Photoperiod on the Frequency of Sexual Embryo Sacs in Facultative Apomictic Buffelgrass*, Euphytica 54: 141–145 (1991).

Jankun, A. et al., *Apomixis at the Diplois Level in Sorbus eximia* (*Embryological Studies in Sorbus 3*), Pt. Praha 60: 193–213 (1988).

Jefferson, R. A. et al., *The Potential Impacts of Apomixis: a Molecular Genetics Approach, In Sobral BWS* (ed), The Impact of Plant Molecular Genetics, Birkhauser, Boston (1996).

Koltunow, A.m. et al., *Apomixis: Molecular Strategies for the Generation of Genetically Identical Seeds Without Fertilization*, Plant Physiology 108: 1345–1352 (1998).

Knox, R. B., *Apomixis: Seasonal and Population Differences in a Grass*, Science 157:325–326 (1967).

Knox, R. B. et al., *Experimental Control of Apsporous Apomixis in a Grass of the Andropogoneae*, Botanisk Notiser 116: 127–141 (1963).

Leblanc, O. et al., *Megasporogenesis and Megagametogenesis in Several Tripsacum species* (*Poaceae*), American Journal of Botany 82: 57–63 (1995).

Leblanc, O. et al., *Timing of Megasporogenesis in Tripsacum species* (*Poaceae*) *as Related to the Control of Apomixis and Sexuality*, Polish Botanical Studies 8: 75–81 (1994).

Marshall, D. R. et al., *The Evolution of Apomixis*, Heredity 47: 1–15 (1981).

Mogie, M., *A Model for the Evlution and Control of Generative Apomixis*, Biological Journal of the Linnean Society 35 : 127–153 (1988).

Mujeeb–Kazi, A., *Apomictic Progeny Derived from Intergeneric Hordium–Triticum Hybrids*, The Journal of Heredity 72: 284–285 (1981).

Mujeeb–Kazi, A., *Apomixis in Trigeneric Hybrids of Triticum aestivum/Leymus racemosa/Thinopyrum elongatum*, Cytologia 61: 15–18 (1996).

Naumova, T.N. et al., *Quantitative Analysis of Aposporous Parthenogenesis in Poa pratensis Genotypes*, Acta Botanica Neerlandica 42: 299–312 (1993).

Naumova, T.N. et al., *Ultrastructural Characteristics of Apospory in Panicum maximum*, Sexual Plant Reproduction 8: 197–204 (1995).

Nogler, G.A., *Genetics of Gametophytic Apomixis—a Historical Sketch*, Polish Botanical Studies 8: 5–11 (1994).

Nordborg, B., *Embryological Studies in the Sanguisorba Minor Complex* (*Rosaceae*), Botaniska Notiser 120 109–119 (1967).

Ozians–Akins, P. et al., *Transmission of the Apomictic Mode of Reproduction in Pennisetum: Co–Inheritance of the Trait and Molecular Markers*, Theoretical and Applied Genetics 85: 632–638 (1993).

Peacock, J., *Genetic Engineering and Mutagenesis for Apomixis in Rice*, In. Wilson K.J., ed. Proceedings of the International Workshop on Apomixis in Rice, Changsha, China. New York: Rockefeller Foundation 11–22 (1993).

Peel, Michael D. et al, *Megasporocyte Callose in Apomictic Buffelgrass, Kentucky Bluegrass, Pennisetum squamulatum Fresen. Tripsocum L., and Weeping Lovegrass*, Crop Science, vol. 37, No. 3.

Peel, Michael D., et al., *Meiotic Anomalies in Hybrids Between Wheat and Apomictic Elymus rectisetus* (*Noes in Lehm.*) *A. Löve & Connor*, Crop Sci. 37, 717–723 (1997).

Saran, S. et al., *Environmental Control of Reproduction in Dichanthium intermedium*, Journal of Cytology and Genetics 11:22–28 (1976).

Sherman, R.A. et al., *Apomixis in Diploid X Triploid Tripsacum dactyloides hybrids*, Genome 34: 528–532 (1991).

Vielle Calzada J–P et al., *Apomixis: the Asexual Revolution*, Science 274: 1322–1323 (1996).

Quarin, Seasonal changes in the incidence of apomixis of iploid, triploid, and tetraploid plants of *Paspalum cromyorrihizon*. Euphytica. vol. 35, pp. 515–522, (Abstract only) 1986.

That, New developments in hybrid rice. International Rice Commission Newsletter, vol. 42, pp. 28–34. (Abstract only) 1993.

Bashaw et al., Apomictic grasses. In: Principles of Cultivar Development vol. 2, Fehr (ed.), Macmillan Publishing Company, New York, pp. 40–82. 1987.

Hanna et al., Apomixis: Its identification and use in plant breeding. Crop Science. vol. 27, pp. 1136–1139. 1987.

Hovin et al., Apomixis in Kentucky bluegrass. Crop Science. vol. 16, pp. 635–638. 1976.

* cited by examiner

METHODS FOR PRODUCING APOMICTIC PLANTS

CROSS-REFERENCE TO RELATED APPLICATIONS

This application is a continuation of application Ser. No. 09/018,875, filed Feb. 5, 1998, which claimed the benefit of application Ser. No. 60/037,211, filed Feb. 5, 1997.

BACKGROUND OF THE INVENTION

This invention relates to methods for producing plants that genetically clone themselves through their own seed (gametophytic apomicts) from plants that normally reproduce sexually. More particularly, the invention relates to processes that include (a) selection of two or more sexual lines that express reproductive phenotypes divergent from each other, which may in some cases require plant breeding and selection to obtain sufficient degrees of divergence, (b) hybridization among plants divergent in reproductive phenotype, and (c) amphiploidization (doubling of chromosomes) either before or after hybridization.

It is likely that apomixis has a greater potential for increasing yields of food, feed, and fiber than any other plant mechanism. Apomixis occurs in about 0.3% of flowering plant species. The present patent application describes methods for making sexual plants apomictic without crossing them to wild apomictic relatives or using mutagenic procedures, both of which have been attempted but with disappointing results. The procedures described herein mimic how apomixis evolved in nature (J. G. Carman, Asynchronous Expression of Duplicate Genes in Angiosperms May Cause Apomixis, Bispory, Tetraspory, and Polyembryony, 61 Biol. J. Linnean Soc. 51–94 (1997) (incorporated herein by reference; hereinafter, "Linnean"), and enable persons skilled in the art of plant breeding and genetics to convert inbred crops, including wheat, barley, and rice, into apomictic hybrid crops with potential yield increases of 10 to 30% over currently used inbred varieties. Crops currently used as hybrids, such as maize, may also be made apomictic. Apomictic hybrids of either inbred or typically hybrid crops will behave as hybrids only in terms of their superior yields. The seed of apomictic hybrids are genetic clones of the mother hybrid, i.e. genetic segregation does not occur. Thus, farmers could use a small fraction of their harvest for seed and expect high yields and uniformity year after year. This would allow hybrids, the seed of which is typically very expensive, to be used in impoverished nations for the first time, which could contribute substantially to another "green revolution".

Gregor Mendel conducted, unknowingly, the first genetic experiments with gametophytic apomicts (plants that produce seed asexually). He reported the successful crossing of different Hieracium lines but commented on the extreme difficulty of preventing self fertilization. What he thought was high frequency accidental selfing (in his facultatively-apomictic Hieracium lines) was actually high frequency apomictic seed formation. To add to his frustration, Mendel failed to observe segregation among the $F_2$s of the few $F_1$s he managed to produce. His $F_2$s were actually apomictic clones of his $F_1$s, and they invariably expressed their respective $F_1$, phenotypes (S. E. Asker & L. Jerling, Apomixis in Plants (CRC Press, 1992) (hereby incorporated by reference; hereinafter, "Asker & Jerling").

Several thousand species of Hieraclum had been described by the time Mendel hybridized members of this agamic complex. This pronounced polymorphy, and that observed in other agamic complexes (Antennaria, Erigeron, Taraxacum, Potentilla), coupled with Mendel's results in producing new polymorphs by crossing facultative apomicts, led early geneticists to conclude that hybridization in agamic complexes is a major mechanism of speciation. Evidence for this conclusion is replete, e.g. in Amelanchier and Crataegus (C. S. Campbell & T. A. Dickinson, Apomixis, Patterns of Morphological Variation, and Species Concepts in Subfam. Maloideae (Rosaceae), 15 Systematic Bot. 124–25 (1990) (incorporated herein by reference), in Antennaria (Bayer et al., Phylogenetic Inferences in Antennaria (Asteraceac: Gnaphalieae) Based on Sequences from the Nuclear Ribosomal DNA Internal Transcribed Spacers (ITS), 83 Amer. J. Bat. 516–527 (1996) (incorporated herein by reference), in numerous agamic grass complexes (E. A. Kellogg, variation and Species Limits in Agamospermous Grasses, 15 Systematic Bot. 112–23 (1990) (incorporated herein by reference), in Rubus (Nybom, Evaluation of Interspecific Crossing Experiments in Facultatively Apozmictic Blackberries (Rubus Subgen. Rubus). Using DNA Fingerprinting, 122 Hereditas 57–65 (1995) (incorporated herein by reference), in Taraxacum (Richards, The origin of Taxaxacum agamospecies, 66 Biol. J. Linnean Soc. 189–211 (1973) (incorporated herein by reference), and others. In contrast, two conflicting opinions soon developed among early geneticists regarding the role of hybridization in the origins of apomixis. Strausburger, Zeitpunkt der Bestimmung des Geschlechtes, Apogamie, Parthenogenesis und Reduktionsteilung, 7 Hist. Beitr. 1–124 (1909) (incorporated herein by reference), Ostenfeld, Experiments on the Origin of Species in the Genus Hieraci (Apogamy and Hybridism), 11 New Phytol. 347–54 (1912) (incorporated herein by reference), and Holmgren, Zytologische Studien uber die Fortpflanzung bei den Gattungen Erigeron und Eupatorium, 59 Kgl. Sven Vetenskapsakad. Ak. Handl. No. 7, 1–118 (1919) (incorporated herein by reference) believed apomixis is controlled by genetic factors (genes) specific to apomixis and is not a consequence of hybridization. In contrast, A. Ernst, Bastardierung als Ursache der Apogamie im Pflanzenreich, Fischer, Jena (1918) (incorporated herein by reference), believed that the cytological anomalies of reproduction responsible for apomixis are extensions of the genomic disturbances observed in wide hybrids.

Ernst amassed much evidence to support his hybridization hypothesis, which included the facts What apomicts have high chromosome numbers (they are generally polyploid), that agamic complexes are highly polymorphic, and that the sex cells of apomicts often degenerate in a manner observed in interspecific hybrids. A major tenet of Ernst's hypothesis, and the one which soon caused its widespread dismissal (and continues to cause its legitimate dismissal today), was that hybrids form a continuum from fully functional sexual reproduction, to apomixis, and finally to vegetative reproduction. Where a hybrid fit on the continuum depended on how closely related the parent species are, e.g. if the parents are closely related, the hybrid will reproduce sexually, if the parents are moderately related, the hybrids may tend to be apomictic, if the parents are distantly related, the hybrids may tend to reproduce by vegetative propagation. Thus, according to Ernst, apomixis arises only in wide hybrids. Ernst did not identify mechanisms to support a hybrid origin for apomixis other than the wideness of the cross.

Ernst's hypothesis received support in the 1920s and 1930s (Harrison, The Inheritance of Melanism in Hybrids Between Continental *Tephrosia crepuscularia* and *Britisht bistortata*, with Some Remarks on the Origin of Parthenogenesis in Interspecific Crosses, 9 Genetika 4467 (1927)

(incorporated herein by reference); G. L. Stebbins, Cytology of Antennaria. II. Parthenogenetic Species, 94 Bot. Gaz. 322–45 (1932) (incorporated herein by reference)), but most geneticists had rejected it by the time Ake Gustafsson published his comprehensive treatise, A Gustafsson, Apomixis in Higher Plants, I. The Mechanism of Apomixis, 42 Lunds Universitets Arsskrift 1–67 (1946); A Gustafsson, Apomixis in Higher Plants, II. The Causal Aspect of Apomixis, 43 Lunds Universitets Arsskrift 69–179, (1947); A Gustafsson, Apomixis in Higher Plants, III. Biotype and Species Formation, 43 Lunds Universitets Arsskrift 181–370 (1947) (incorporated herein by reference). In this treatise, Gustafsson concluded; "In no case is it proved that hybridization itself has been able to produce apomixis. On the contrary, it is certain that the apomictic method of reproduction has in many cases arisen within a species population." The fact that some apomicts are autopolyploid, which was well documented by 1946, legitimately squelched any perceived requirement for wide hybridization. Hence, Ernst's hypothesis collapsed because it claimed that the cytological mechanisms of apomixis are extensions of the cytological abnormalities observed during gamete formation in wide hybrids, which, by definition, contain grossly divergent genomes that prevent normal chromosome pairing during meiosis. We know today that this is not the case, i.e. chromosome pairing in many apomicts is normal. Since Gustafsson's treatise, few geneticists have suggested that the role of hybridization in agamic complexes exceeds that of speciation among taxa already containing a genetically-determined predisposition for apomixis. Dissecting this genetic predisposition is being attempted but is proving to be a formidable task.

Few genetic analyses of apomixis were conducted prior to Gustafsson's treatise, and these lacked the numbers of progeny required to draw specific conclusions (Asker & Jerling). Nevertheless, they suggested to Gustafsson that apomixis is caused by interbalanced systems of recessive genes. Gustafsson defended this view by citing examples in (a) Parthenium, Poe, and Potentilla, where embryo sac formation and parthenogenesis are under independent genetic control, and (b) Poa, Potentilla, and Rubus, where hybrids between two apomicts or between an apomict and a sexual parent are either sexual or apomictic with no clear pattern as to the outcome (suggestive of many recessive genes). In Rubus, sexual $F_1s$ had been produced from apomictic parents, and these $F_1s$ produced a low percentage of apomictic $F_2s$, which again suggested segregation for multiple recessive factors.

Another realm of apomixis research that has produced ambiguities involves the effects of artificially changing the ploidy of apomicts. The general trend is for apomixis to intensify when the ploidy of an apomict is artificially increased. However, exceptions in Potentila, Taraxacum, Paspalun, and Poa have been found in which artificially-induced increases in ploidy cause (a) haploparthenogenesis, in which reduced eggs form and develop without fertilization, (b) $B_{III}$hybridization, in which unreduced eggs are fertilized, and (c) complete restoration of sexuality. Sexuality has also been restored in apomictic Poa by haploidization. Concerning such ambiguities, Asker and Jerling concluded: "Our difficulties in explaining the 'breakdown of apomixis' remain connected with our ignorance concerning regulation . . . " Such ambiguities persuaded Gustaffson to reject simple dominance models for the inheritance of apomixis. He saw little evidence for them and was unconvinced by such claims in Dryopteris, Hieraciur, Hypericum, Potentilla, and Sorbus. In each case, Gustaffson provided reasonable alternatives for the published claims.

Distorted segregation ratios can also hinder genetic analyses of apomixis. Certain apomicts in Dichanthium and Themeda tend to be sexual when grown in long days and apomictic when grown in short days (Asker & Jerling). Nevertheless, replicated studies with consistent segregation ratios have now been conducted in Panicum (Asker & Jerling), Tripsacum (O. Leblanc et al., Detection of the Apomictic Mode of Reproduction in Maize-Tripsacum Hybrids Using Maize RFLP Markers, 90 Theor. Appl. Genet. 1198–1203 (1995) (incorporated herein by reference), and Brachiaria (Valle & Miles, Breeding of Apomictic Species, in Y. Savidan & J. G. Carman, Advances in Apomixis Research (FAO, Rome, in press) (incorporated herein by reference), and each study suggested that apomeiosis (detected cytologically) is controlled by a single dominant allele. However, other recent studies challenge this conclusion, e.g. the apomeiosis "allele" in the Tripsacum accession studied by O. Leblanc et al., 90 Theor. Appl. Genet. 1998–1203 (1995), is part of a large linkage group in which recombination is suppressed, and a similar linkage group appears to exist in apomictic Pennisetum (Grimanelli et al., Molecular Genetics in Apomixis Research, in Y. Savidan, J. G. Carman, Advances in Apomixis Research (FAO, Rome, 1998) (in press, incorporated herein by reference)). These linkage groups may contain multiple genes required for apotreosis (Grimanelli et al., Mapping Diplosporous Apomixis in Tetraploid Tripsacum: One Gene or Several Genes?, Heredity (1998) (in press, incorpor ated herein by reference)).

Two research groups are presently attempting to introgress apomixis into maize from Tripsacum, and neither has reported its expression in addition lines with less than nine Tripsacum chromosomes. In one group, two apomictic maize triploids containing nine Tripsacum chromosomes (3x+9) were produced. Cytogenetic and molecular studies indicated that the nine Tripsacum chromosomes in each line were probably the same (B. Kindiger et al., Evaluation of Apomictic Reproduction in a Set of 39 Chromosome Maize-Tripsacum Backcross Hybrids, 36 Crop Sci. 1108–13 (1996) (incorporated herein by reference)). A third triploid addition line, again with nine Tripsacum chromosomes (3x+9), was produced by the same group. However, many of the nine chromosomes in this line differed from the nine chromosomes of the two former lines. The maize chromosomes were the same for all three lines. The latter 3x+9 plant was also apomictic, but the frequency of apomixis was only 10 to 15%, compared with 95 to a 100% for the two former lines (Sokolov et al, Perspectives of Developing Apomixis in Maize, Priority Directions of Genetics, Russia (1997) (progress report; incorporated herein by reference)). These data, and unpublished findings from the other group attempting to transfer apomixis to maize (Grimanelli et al., Molecular Genetics in Apomixis Research, in Y. Savidan, J. G. Carman, Advances in Apomixis Research (FAO, Rome, 1998) (in press)), suggest a complex mode of inheritance for apomixis. In another study, sexual T. dactyloides diploids were crossed with highly apomictic T. dactyloides triploids to produce aneuploids. All but three of 46 $F_1s$ showed tendencies for apotmeiosis (determined cytologically). However, the highly apomeiotic $F_1s$ contained seven or more additional chromosomes (above the diploid level), and all $F_1s$ with chromosome numbers near the diploid level were sexual (Sherman et al., Apomixis in Diploid X Triploid Tripsacum dactyloides Hybrids, 34 Genome 528–32 (1991) (incorporated herein by reference)), which suggests complex inheritance. Finally, apomixis in artificially produced Tripsacum triploids cosegregated with five Tripsacum linkage groups syntenic with regions from three maize chromosomes (Blakey et al, Co-segregation of DNA Markers with Tripsacum Fertility, 42 Maydica 363–69 (1997) (incorporated herein by reference)), which further discredits a simple inheritance mechanism for the control of apomixis (at least when attempting to transfer the apomixis mechanism to other species or other lines within a species). It is reasonable to assume that a major gene (a regulatory or controlling gene) could prevent apomixis from occurring when in the recessive condition, thus making apomixis appear to be under simple genetic control. However, such gene(s) belong to many genes required for the expression of apomixis and will not confer apomixis to other species by themselves (Linnean). The studies just reviewed infer: (a) multiple genes are required for apomixis, (b) genes affecting facultativeness may behave additively, (c) some Tripsacum chromosomes affect facultativeness more than others, and (d) alleles from at least three maize chromosomes fail to substitute for their homeologous (syntenic) counterparts from Tripsacum in conferring apomixis.

Meiotic mutants are central to the simple inheritance hypotheses (Linnean). Recent mutation hypotheses suggest apomixis is not expressed unless appropriate meiotic mutations are combined with an appropriate polygenic predisposition (Mogie, The Evolution of Asexual Reproduction in Plants (1992) (incorporated herein by reference); Grimanelli et al, Molecular Genetics in Apomixis Research, in Y. Savidan, J. G. Carman, Advances in Apomixis Research (FAO, Rome, 1998) (in press)). However, recently obtained evidence indicates that the alleles thought to be mutations are actually part of the polygenic predisposition and are required for sexual reproduction in marginal habitats. What has not been previously appreciated, but which is shown herein, is that it is the union of divergent ecotypes (interracial or interspecific) through secondary contacts that permits apomixis to arise (see also Linnean).

In view of the foregoing, it will be appreciated that providing methods for producing apomictic plants would be a significant advancement in the art.

BRIEF SUMMARY OF THE INVENTION

It is an object of the present invention to provide methods for creating apomictic plants from sexual plants without using mutagenic procedures or plants that are already apomictic.

Additional objects and advantages of the invention are set forth in the detailed description or will be appreciated by the practice of the invention.

To address the foregoing objects, and in accordance with the invention as described herein, the present invention provides methods for producing apomictic plants from two or more sexual plants of the same or related species.

One step of the method involves obtaining two sexual lines whose female reproductive phenotypes differ such that under the same environmental conditions (day length, light intensities, temperature regimes, etc.) an appropriate degree of asynchrony in female developmental schedules between the two lines occurs. Appropriate degrees of asynchrony include but are not limited to situations in which megasporogenesis in one line is initiated at about the same time embryo sac formation is initiated in the other line relative to the development of nongametophytic ovule and ovary tissues (nucellus, integuments, pericarp, etc) and other phenological factors such as photoperiod-regulated floral induction times. The accelerated line (line undergoing embryo sac development) would have already accomplished floral induction and megasporogenesis.

Another step of the method involves making amphiploids of the appropriately-divergent sexual lines (using standard chromosome doubling techniques), if they are not already polyploid, and hybridizing the two sexual amphiploid lines to induce apomixis. Hybridization may precede amphiploidization. In such cases, the amphiploidization may involve standard mitotic spindle inhibitors, such as colchicine, or rely on the formation of $B_{III}$ hybrids (fertilization of an unreduced egg) to produce apomictic triploids. Other processes are included in the examples described below.

DETAILED DESCRIPTION

Figure 1:
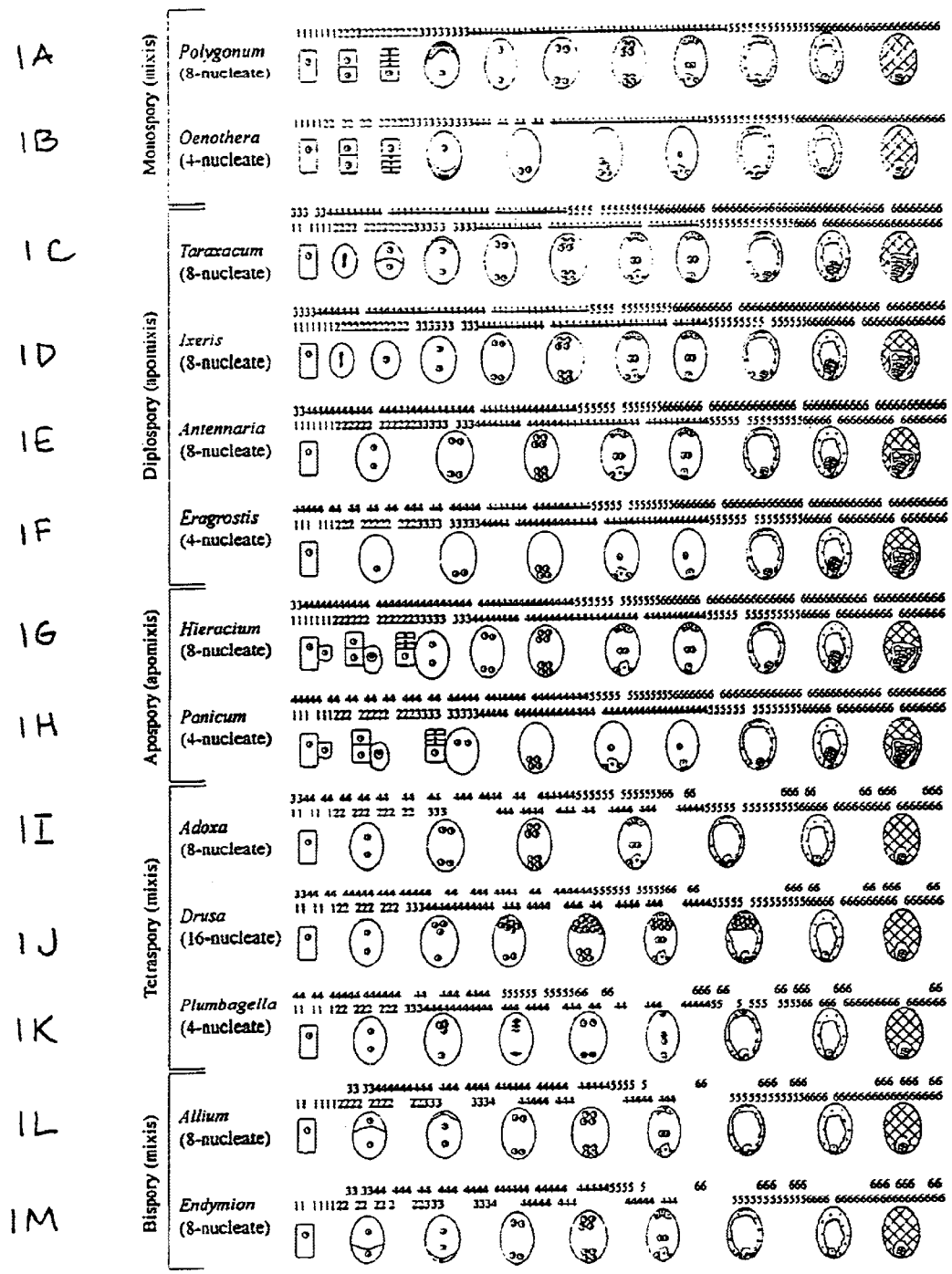
FIGS. 1A–M show schematic representations of the development of representative types of sexual (mixis) and apomictic embryo sacs (see B. M. Johri et al., Comparative Embryology of Angiosperms, Vol. 1 and 2 (Springer-Verlag, 1992); Asker & Jerling). Polygonum-type development is the norm and is expressed exclusively in >99% of all angiosperm species. The horizontal row(s) of numbers associated with each developmental type denote stage-specific gene expression: (1) premeiotic interphase and early meiotic prophase (crossing-over and envelopment of MMCs in callose), (2) meiotic divisions, (3) megaspore maturation (digestion of callose from and initial vacuolization of the surviving megaspore), (4) embryo sac development, (5) double fertilization and early endosperm formation, and (6) embryogenesis (usually initiated after early endosperm formation). Parallel rows of numbers indicate hypothesized asynchronous expression of duplicate genes, the members of which originate from different genomes in polyploids or segments of different ancestral genomes in paleopolyploids. Gaps in the numbers represent mutations (mostly null alleles) and deletions. Note that gaps are most prevalent among the palecpolyploid polysporic types and least prevalent among the polyploid apomictic types. Some null-allele formation probably enhances seed set in apomicts. The arbitrary elimination of gene duplications in developmentally-asynchronous polyploids and paleopolyploids appears to represent a major evolutionary process in which new reproductive types (apomixis, polyspory, and polyembryony) evolve (Linnean).

Before the present methods for producing apomictic plants are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

Historically, the term apomixis, when applied to flowering plants (angiosperms), has included various forms of vegetative propagation. The term apomixis is limited herein, however, to those processes routinely resulting in asexual reproduction without conjunction of gametes of opposites sexes (parthenogenesis) from unreduced eggs. These processes are frequently described as forms of gametophytic apomixis and involve anomalies that disrupt normal ovule development. In contrast, bispory and tetraspory (collectively referred to as polyspory herein) also disrupt ovule development, but normal, reduced eggs that require fertilization are formed (FIGS. 1J–M). Cytological similarities between apomixis and polyspory have recently been identified (U.S. Ser. No. 60/037,211; see also Linnean). These similarities suggest commonalities in the origins of apomixis and polyspory.

Megasporogenesis (female meiosis) in angiosperms occurs in megaspore mother cells (MMCs), and the female gametophyte (embryo sac) normally develops from one of four meiotic products (megaspores). Most angiospenmous embryo sacs are eight-nucleate (FIG. 1A) and contain an egg (fertilized to form the embryo), two synergid cells, a central cell composed of two polar nuclei (fertilized to form the endosperm), and three antipodal cells (Polygonum-type embryo sac). Each nucleus is originally haploid and is derived from the nucleus of the surviving megaspore through three sequential endomitotic divisions (FIG. 1A). Apomixis interrupts this process, resulting in diplospory (FIGS. 1C–F) or apospory (FIGS. 1G–H).

In the form of apomixis known as diplospory, an unreduced embryo sac forms from a MMC in which meiosis is disturbed and replaced by precocious embryo sac formation (FIGS. 1C–F). The completion of embryo sac formation is also precocious, and the unreduced egg divides parthenogenetically to form a proembryo, often prior to fertilization (e.g., Linnean). The form of apomixis known as apospory is similar to diplospory except the unreduced embryo sac forms from a somatic cell of the ovule wall near the MMC (FIGS. 1G–H). During apospory, either the meiotic MMC or the young sexual embryo sac aborts and is replaced by one or more aposporic embryo sacs (Asker & Jerling), which also tend to develop precociously (Linnean; Asker & Jerling). Hence, both of these anomalies result from the premature expression of genes required for embryo sac formation, and most if not all apomicts are facultatively sexual, which means sexuality has been retained during their evolution and is occasionally expressed (Linnean; Asker & Jerling).

Tetraspory, in which meiotic nuclear divisions (karyokineses) occur but cell divisions (cytokineses) do not (FIGS. 1I–K; M. T. M. Willemse & J. L. van Went, The Female Gametophyte, in B. M. Johri, Embryology of Angiosperms 159–96 (Springer-Verlag, 1984), incorporated herein by reference; B. M. Johri et al, Comparative Embryology of Angiosperms, Vol. 1 and 2 (Springer-Verlag, 1992) (incorporated herein by reference)), has also been attributed to a "precocious gametophytization" of the MMC (E. Battaglia, The Evolution of the Female Gametophyte of Angiosperms: An Interpretative Key, 47 Annali di Botanica 7–144 (1989), incorporated herein by reference)). Both tetrasporic and diplosporic MMCs undergo vacuolization, which normally occurs in the surviving sexual megaspore during the onset of embryo sac formation. Such vacuolization also occurs in aposporous initials (Linnean). In both diplospory and tetraspory, embryo sac formation continues without interruption. In normal species, megasporogenesis and embryo sac development are temporally separated during which time callose (a $\beta$,1–3 glucan) in the walls of the surviving megaspore is catabolized (Linnean).

The MMC walls of diplosporic and tetrasporic species lack callose, which normally envelops MMCs of monosporic and bisporic species during early prophase (FIGS. 1A–B, L–M) and is deposited in the cross walls during megasporogenesis (Linnean). These deposits are catabolized following meiosis, which permits rapid megaspore expansion at the onset of embryo sac formation. The absence of callose in diplosporic and tetrasporic species permits the precocious expansion of MMCs (FIGS. 1C–F, I–K) and is further evidence of MMC gametophytization (Linnean; E. Battaglia, 47 Annali di Botanica 7–144 (1989); M. D. Peel et al, Megasporocyte Callose in Apomictic Buffelgrass, Kentucky Bluegrass, Pennisetum squamulatum Fresen, Tripsacum L. and Weeping Lovegrass, 37 Crop Science 724–32 (1997) (incorporated herein by reference)). Forms of polyspory, like forms of apomixis, are derived anomalies of widespread polyphyletic origin (Linnean).

There are many forms of polyembryony, which is the formation of more than one embryo per ovule (synergid and antipodal embryony, cleavage polyembryony, adventitious embryony) (Linnean). Like apomixis and polyspory, the various forms of polyembryony are polyphyletically derived and involve temporally and spatially-misplaced developmental programs.

Phylogenetic and cytological studies shed light on the origins of apomixis. Cytological comparisons indicate that some apomictic types resemble unusual sexual types more than other apomictic types, e.g. Adoxa-type tetraspory (sexual) is identical to Antennaria-type diplospory except the nuclear divisions leading to a tetranucleate embryo sac are meiotic in tetraspory but mitotic in Antennaria-type diplospory (FIGS. 1E & 1I). Likewise, Ixeris-type diplospory (FIG. 1D) is identical to sexual bispory (FIGS. IL & 1M) except meiosis I fails in the former. Both Ixeris-type diplospory and bispory (and apospory and tetraspory) occur in the genus Erigeron. Phylogenetic data have been analyzed and it has been found that apomzxis and polyspory often occur together at the generic and familial levels (highly significant associations). Likewise, preleptotene chromosome condensations and the formation of nonfunctional megasporocytes that are subsequently replaced by functional megasporocytes occur in species closely related to apomictic or polysporic species, which also suggests similar mechanisms of evolution.

High chromosome base numbers ($x \geq 10$) usually indicate paleopolyploidy, which means polyploidy followed by diploidization with or without ascending or descending aneuploidy. Multiple base numbers per genus also reflect paleopolyploidy. It has been found that chromosome base numbers for 80% of all genera identified as containing apomictic, polysporic, or polyembryonic species. Statistical analyses indicated that polysporic and polyembryonic species are generally paleopolyploid, while apomicts, which are generally polyploid (Asker & Jerling), often contain primary genomes. Furthermore, genera with polysporic but not apomictic species had more x values per genus (2.7±0.4 SE) than genera with apomictic but not polysporic species (1.7±0.1). This means apomicts tend to have balanced sets of duplicate genes (primary genomes) and polysporic and polyembryonic species usually have imbalanced sets of genes (paleopolyploid genomes, i.e. partially duplicated or triplicated due to aneuploidy). Hence, in the present invention it is shown that in polyploids composed of reproductively divergent ecotypes (a) interactions among balanced genomes (containing complete sets of reproductive genes) are required for certain female developmental sequences, e.g. megasporogenesis, etc., to be completely replaced by developmental sequences that normally occur later in development, such as occurs in apomixis, (b) interactions among unbalanced "paleopolyploid" genomes containing incompletely-duplicated or triplicated sets of reproductive genes are required for only portions of certain female developmental sequences to be asynchronously replaced or duplicated by other portions of developmental sequences, such as occurs during polyspory, polyembryony, preleptbtene condensations, and MMC replacements, and (c) apomixis, with its long-term reproductive stability, may, when influenced by paleopolyploid processes, be an evolutionary springboard (rather than a dead end) in the evolution of normal and developmentally-novel paleopolyploid sexual species and genera.

Heterokaryon studies with yeast shed light on the types of developmental mechanisms that may cause apomixis, polyspory, ard polyembryony. Entire cell cycle stages are skipped when yeast cells in G1 are fused with cells in S-phase, i.e. G1 chromosomes replicate precociously. The rate of initiation of replication deperds on the S:G1 nucleus ratio in the heterokaryon. In mitotic yeast cells fused with interphase cells, the interphase nuclei (all stages) prematurely enter mitosis (B. Lewin, Genes V, (Oxford University Press, 1994) (incorporated herein by reference)).

Apomixis may occur in an analogous manner. If embryo sac development signals from one genome are superimposed on megasporogenesis signals from another genome, meiosis may be skipped (diplospory) or embryo sac development may be ectopic (apospory). Accordingly, apomictic-like tendencies occur in polyploids only if major differences in timing of megasporogenesis and embryo sac development (relative to development of nongametophytic ovule and ovary tissues) exist among the ancestral ecotypes or species (Table 1). Such natural variation might only be frequently found in highly cosmopolitan species, i.e. species with broad latitudinal and ecological distributions.

Table 1 depicts a model of how asynchronously-expressed duplicate genes cause diplospory and apospory in polyploids containing two genomes divergent in the temporal expression of female developmental schedules (floral induction, megaspore formation, and gametophyte development). Italicized developmental phases encoded by genome I are skipped because of precociously-expressed check-point genes from genome II.

TABLE 1

| Genome | Developmentally-critical stages* | | | |
|---|---|---|---|---|
| | 1 | 2 | 3 | 4 |
| Genome I (unmodified) | Archespore | Meiosis | Embryo sac | Double fertilization/ early embryony |
| Genome I (modified) | | Embryo sac | Double fertilization/ early embryony | Fertilization of central cell only |
| Genome II | Meiosis | Embryo sac | Double fertilization/ early embryony | Fertilization of central cell only |

*Ovary development is initiated by a compromise between developmental signals from genome I, which evolved in short days and long seasons (lower latitudes), and genome II, which evolved in long days and short seasons (higher latitudes). Thus, the initiation and pace of ovary development assumes an "intermediate phenotype" in a manner similar to other intermediate phenotypes observed in amphiploids derived from morphologically-distinct parents (leaf lengths and widths, plant height, etc.).

1. At the beginning of stage 1, genome II produces precocious signals for meiosis, which fail because the archespore mother cell has not yet formed, i.e. it develops at an intermediate rate dictated by the intermediate phenotype.
2. At the beginning of stage 2, end-of-meiosis check-point signals from genome II terminate meiosis and synchronize genome I with genome II in a manner similar to that observed in asynchronous yeast heterokaryons (reviewed herein). If meiosis is successfully terminated, one of several forms of diplospory (FIG. 1) occurs, i.e. an embryo sac forms directly from the megasporocyte (Antennaria-type diplospory) or young female meiocyte (Taraxacum or Ixeris-types of diplospory). If meiosis is unsuccessfully terminated, apospory (FIG. 1) may occur, i.e. one or more embryo sacs may form from adjacent nucellar cells. This occurs primarily in species containing multiple or ill-defined archegonial cells. In both apospory and diplospory, a genetically unreduced embryo sac develops. Development of the nongametophytic tissues of the ovule and ovary continues to occur according to the intermediate-phenotype (delayed) schedule. In contrast, gametophyte (embryo sac) development continues to occur precociously because the embryo sac development genes of genome I (in the embryo sac only) are synchronized with those of genome II.
3. Signals from the two synchronized genomes induce egg formation and parthenogenesis, both of which occur precociously in most apomicts relative to the development of nongametophytic tissues of the ovule and ovary.
4. Pollination occurs according to the intermediate phenotype schedule, but the egg is no longer receptive and in many cases has already divided. The central cell, if not autonomous, is fertilized, and the endosperm and parthenogenetic embryo develop.

This duplicate-gene asynchrony hypothesis explains at a rudimentary level many genomic peculiarities of species exhibiting reproductive anomalies as well as many inconsistencies in the apomixis literature. For example, apomixis, polyspory, and polyembryony are rare but tend to occur together in cosmopolitan families because sufficient ecotypic variation in reproductive start-times, etc., is rare in most families but is high in cosmopolitan families. Sexual reproduction of the monosporic Polygonum-type occurs facultatively in apomictic and polysporic species (Linnean) because, barring deletions or mutations, each parental genome contains genes required for normal reproduction, and growing conditions may occasionally favor the expression of one genome over the other causing sexual development to occur, as occurs in Dichanthium, Themeda, and numerous other apomicts. Facultativeness is influenced by (a) differential silencing of genomes, which could be caused by differences in genetic background, or (b) environmental factors that reduce the degree of asynchrony by accelerating or decelerating gene expression from one genome (photoperiod or temperature response, etc.) relative to that of another, thus allowing sexual development to occur. Polyspory and polyembryony result from the competitive expression of grossly imbalanced genomes (incomplete sets of reproductive genes) in which some checkpoint systems are missing. In contrast, competitive expression among genomes is terminated by checkpoint genes in apomicts, which generally contain balanced sets of reproductive genes, thus allowing a smooth transition to apomixis (Table 1). At least one of the two parental genomes of an apomict must have sufficient DNA to extend the duration of reproductive development (meiotic durations, etc) such that sufficient asynchrony can be expressed. Hence, apomixis is seldom found in annuals, which have little DNA and rapid meioses. Likewise, polyhaploidy may obliterate asynchrony causing a reversion to sexuality. Apomixis is much more prevalent among outcrossing species than inbreeding species because they are more prone to form interecotypic or interspecific polyploids when secondary contacts occur, e.g. during the frequent climatic shifts associated with the eight major glaciations and numerous minor glaciations of the Pleistocene (L. A. Frakes et al., Climate Modes of the Phanerozoic (Cambridge university Press, 1992) (incorporated herein by reference)). Likewise, more apomicts are allopolyploid than autopolyploid because polyploidization, which is generally essential to the asynchronous expression of different genomes with respect to female development (Linnean), by $B_{III}$ hybrid formation is expected to occur more frequently in interspecific hybrids than interracial hybrids. Likewise, the chances of $B_{III}$ hybrid formation occurring in mostly sterile interecotypic or interspecific $F_1$ hybrids that are annual is low compared to those that are perennial, which flower every year for many years. This factor further limits the chances of annuals becoming apomictic and further explains the low frequency of naturally-occurring apomictic annuals. Finally, ambiguous outcomes regarding the sexuality of progeny are expected when an apomict is crossed with a sexual or with another apomict, regardless of the closeness or wideness of the cross. The mode of reproduction expressed in the progeny will depend on how the added or removed genome(s) affect asynchrony, and this cannot be predicted without some a priori knowledge of the female developmental schedules encoded by the involved genomes (Linnean). The ability of the duplicate-gene asynchrony hypothesis to adequately explain these many phenomena, which have been considered major inconsistences in the apomixis literature, is strong evidence for its validity.

The distribution patterns of many apomicts indicate a Pleistoceneorigin (G. L. Stebbins, Chromsomal Evolution in Higher Plants (Addison-Wesley, 1971) (incorporated herein by reference); Asker & Jerling), i.e. the geographic distributions and centers of diversity of many apomicts are centered near the margins of the Pleistocene glaciations but their ranges often encompass the ecological ranges of the putative sexual progenitors, which lie north and south of the glacial margins. Eight major glaciations, which covered up to 20% of the earth's surface, occurred during the Pleistocene. These were separated by warm interglacial periods lasting for several thousand to a hundred thousand years each. Likewise, most of the major glacial events consisted of glacial advances interrupted by minor interglacial periods lasting for a few thousand years (L. A. Frakes et al., Climate Modes of the Phanerozoic (Cambridge University Press, 1992). Hence, during the Pleistocene, the northern latitudes of North America and Eurasia were repeatedly deglaciated and revegetated by cosmopolitan taxa capable of adapting to cool climates, long days, and short growing seasons.

A precocious meiosis and embryo sac development in young ovules is an adaptation to short swnmers, in high latitudes. Glacial advances, which followed the numerous interglacial periods, cooled the lower latitudes permitting higher latitude flora to invade lower latitude flora. This provided numerous opportunities for ecotypes with a putatively-precocious female development (from higher latitudes, i.e. temperate to arctic climates) to form polyploids with ecotypes (or different species) with a putatively-delayed female development (from lower latitudes, i.e. tropic to temperate climates). Such polyploids exhibit asynchronous female development, i.e. apomixis.

Another class of adaptations to high and low latitudes includes flowering responses to specific changes in photoperiod during the changing of seasons. Many plants have been categorized according to their responses to photoperiod, e.g. "long day plants" are adapted to higher latitudes and flower in the spring and early summer when days are long, "short day plants" are often found in lower latitudes (tropics) and flower during the tropical "winter" when days are short, "dual-day-length plants" require either short or long days to induce reproductive bud formation followed by long or short days, respectively, to cause the formed buds to mature into flowers, "intermediate-day plants" will not flower if days are too long or too short, and "day-neutral plants" show little adaptation to day length and flower induction occurs under a broad range of day lengths. Several other specialized categories exist. (Salisbury & Ross, Plant Physiology (1992) (incorporated herein by reference)).

Salisbury and Ross selected 85 species, from among approximately 300 species of plants studied to date for flowering responses to different photoperiods. These 85 species distinctly represent the specific photoperiod response categories listed above, and 67 different genera are represented by these 85 species. It is noted herein (for the first time) that 33% of these genera (22 of 67) contain species with female reproductive anomalies (gametophytic apomixis, polyspory, or polyembryony; compare Salisbury & Ross Table 23-1 with the appendix in Linnean). This is a 9-fold increase in the number of genera expected if reproductive anomalies occur independently of adaptations to distinct latitudes, i.e. only 3.8% of genera are known to express reproductive anomalies. Thus, if reproductive anomalies occur independently of distinct adaptations to photoperiod, then only 3.8% (not 33%) of the genera identified as containing species with distinct photoperiod adaptations should have also expressed reproductive anomalies. This 33% is broken down as follows: 12% contain gametophytic apomicts (compared with 1% of all angiospermous genera, i.e. a 12-fold increase), 13% contain polysporic species (compared with 1.6% of all angiospermous genera, i.e. an 8-fold increase), and 7.5% contain polyembryonic species (compared with 1.7% of all angiospermous genera, i.e. a 4.4-fold increase). This highly significant association between genera that contain plants expressing reproductive anomalies and genera that contain plants expressing distinct adaptations to photoperiod (different latitudes) is taken as additional evidence for the duplicate gene asynchrony hypothesis. It is believed that amphiploids containing the genomes of multiple ecotypes divergent in these characteristics (distinctly-different photoperiod responses and distinctly-different times and rates of female development) are apomictic because of asynchronous female development, which causes the formation of unreduced embryo sacs followed by parthenogenesis (Table 1).

The discoveries made in the present invention, as described above, largely invalidate important assumptions currently being relied on by scientists attempting to transfer apomixis to sexual species or to induce its expression de novo by causing mutations. The underlying assumptions for the introgression approach (wide hybridization with an apomictic relative) are that apomixis is controlled by one or a few "apomixis genes" and that these gene(s) can function appropriately in other species. The duplicate-gene asynchrony hypothesis states that apomixis is caused by asynchronous (overlapping) expression of whole sets of genes that are duplicated across interracial (interecotypic) or interspecific genomes and that control entire female developmental sequences in ovules (MMC differentiation, meiosis, megagametophyte development, embryogenesis). Thus, only interactions between gene sets from specifically-divergent genomes will cause an appropriate degree of asyrichrony and induce apomixis. Such specificity varies from species to species, i.e. a gene cassette that induces apomixis in one species may not function appropriately to induce apomixis in another species. Furthermore, it may be impossible to induce apomixis in a particular species whose photoperiod responses and female developmental sequences are average with regard to timing (possibly the vast majority of species) without actually replacing (by plant breeding or genetic engineering) its current female reproductive gene cassettes, which code for temporally-average photoperiod responses and sequences of female development, with two divergent gene cassettes that provide the appropriate degree of asynchrony. It may be argued that one or a few master genes control the timing of these sequences, and that only the master genes need to be transferred, i.e. the master genes of one genome may control the gene cassettes of another genome. However, as noted by Wilson, Breeding for Morphological and Physiological Traits, in K. J. Frey (ed), Plant Breeding II (Iowa State University Press, 1981) (incorporated herein by reference), photoperiod responses are quantitative traits. Furthermore, phylogenetic data indicate that apomixis is lost when cassettes of genes are fragmented by paleopolyploid processes. Thus, while the transfer of apomixis from a wild species to a crop species through wide hybridization and backcrossing may be possible, many previously unforeseen and poorly understood complications are to be expected, including the requirement of transferring many genes possibly from more than one chromosome.

The main assumption of the mutation breeding approach is that apomixis is a single gene or near single gene trait. In the absence of intergenomic asynchrony, only mutations that mimic portions of the many asynchronous interactions responsible for apomixis (all cellular responses from unreduced embryo sac formation through parthenogenesis) can be expected. It is difficult to conceive of an accumulation of mutations that induce an apomixis-like reproductive behavior without deleteriously affecting other cellular, reproductive, or whole plant processes. The asynchrony hypothesis predicts that the mutation approach will meet with major complications.

The main assumption of the sexual plant hybridization approach (A. Ernst, Bastardierung als Ursache der Apogamie im Pflanzenreich, Fischer, Jena (1918)) is that apomixis originates as a fertility restoration mechanism following wide hybridization and amphiploidization. Thousands of wide hybrids and amphiploids have been made by men, but only rarely has apomixis been observed among the progeny (Asker & Jerling; Linnean). The asynchrony hypothesis explains this observation in that the large degree of asynchrony required to induce apomixis is only rarely observed in nature. An example of such rare events in nature is the evolution and radiation of new apomicts in the Rosaceae, Asteraceae, Poaceae, and other families that occurred during the Pleistocene glaciations when grossly different ecotypes of the same species and of closely-related species were repeatedly brought together by climatic shifts where they underwent hybridization and subsequently formed interracial or interspecific apomictic polyploids. Thus, apomixis arises fortuitously only in a very low percentage of man made wide hybrids or amphiploids. In contrast, the asynchrony hypothesis predicts that amphiploids developed from appropriately-selected or bred parental ecotypes or lines (breeding and selection based on cytologically-observable temporal differences in photoperiod responses and timing of female development) will be apomictic.

The invention described herein relies on a specific combination of technologies that explicitly identify, a priori, germplasm that when combined through hybridization and amphiploidization cause gametophytic apomixis to be expressed. The a priori identification of specific combinations of sexual germplasm that confer apomixis when combined as polyploids (by conferring asynchrony in photoperiod responses and other forms of female reproductive timing) differentiates the present invention from the prior art.

The present invention does not depend on the existence of apomixis genes that will be appropriately expressed in different taxa (genomes). In fact, the invention relies on the concept that such genes do not exist. The present invention does not rely on the existence of alleles of genes that when mutated will induce apomixis. Again, the invention relies on the concept that such alleles will probably express deleterious pleiotropic effects when mutated and will not produce desirable apomictic forms. The present invention does not rely on fortuitous or previously-produced wide hybrids that may or may not express apomixis. In contrast, the invention identifies a priori parentage or gene cassettes that when hybridized or combined yield apomixis. The underlying concepts and practices of the claims listed herein are fundamentally different from all other methods of producing apomicts previously conceived or currently in practice throughout the world.

Others have proposed making apozmictic plants by molecular marker assisted introgression of genes for apomixis from wild apomictic relatives to crop species. The data reviewed herein imply that such markers will be of limited use in that the genes they locate will confer apomixis only when numerous other genes are also transferred, which could greatly reduce the agronomic desirability of the crop. These apomixis transfer programs have as long range objectives the identifying and patenting of a universal "apomixis gene" or a universal "apomixis gene cassette". As taught herein, the gene(s) from one genome, which are responsible for conferring apomixis in a polyploid species containing two genomes with different temporal schedules of female development, will only be useful for conferring apomixis in other species or ecotypes if the recipient species contains a genome that is appropriately divergent from the donor genome with regard to the encoding of female developmental schedules. A gene cassette from a single genome probably does not exist for conferring apomixis universally.

The present invention is directed to processes for producing gametophytic apomicts (plants expressing apospory or diplospory) from plants that typically undergo normal sexual reproduction.

The present invention is specifically directed to the production of gametophytic apomicts by combining through hybridization and amphiploidization two or more sexual plants of the same or closely related species that differ in the time and/or duration in which megasporogenesis, megagametogenesis (embryo sac formation), pollination, fertilization, and embryony occur relative to (a) the environmental conditions in which the plants are grown (photoperiod responses, etc.) and (b) gross developmental events in the plants such as ovule initiation, integument growth and development, and pistil length and width.

The present invention is also directed to the amounts of asynchrony in female developmental schedules required among the two or more sexual species used to produce apomictic amphiploids.

The present invention is also directed to the selection pressures and breeding schemes used to create the desired divergence in female developmental schedules reproductive asynchrony) among sexual lines not originally expressing the required female developmental schedules.

It is convenient to separate the process of the present invention into four categories: (a) selection or production of sexual germplasm appropriate for use in producing apomictic plants from sexual plants, (b) hybridization processes, (c) amphiploidization processes, and (d) procedures for verifying expression of apomixis.

Selecting and Breeding Sexual Germplasm for Producinpg Apomicts

A feature of the present invention is the accelerated simulation of processes responsible for the evolution of apomixis from sexual plants in nature. The natural process requires tens of thousands of years, i.e. it may require glaciers to advance, which causes plant populations separated for thousands of years (and adapted to different climates and photoperiods) to be reunited. In the present invention, the duration of the entire process is reduced from tens of thousands of years to only a few years.

A preferred method of selecting germplasm for producing apomictic plants from sexual plants involves the identification of plants of the same species or closely related species that contain ecotypes photoperiodically adapted to broadly-divergent latitudes (long day plants, short day plants, day neutral plants, etc., Salisbury & Ross, Plant Physiology (1992). Many such "cosmopolitan" taxa exist in the Poaceae, Asteraceae, and Rosaceae (Linnean; see examples, infra). Groups of germplasm are selected such that they represent extremes in (a) latitude in which the ecotypes were derived, (b) flowering response to different photoperiods, and c) timing of megasporogenesis, megagametogenesis, and embryony relative to the development of nongametopytic ovule and ovary tissues.

Plant breeding is required as part of the preferred method of obtaining germplasm for producing apomictic plants from sexual plants when appropriate degrees of divergence in female developmental schedules does not exist among currently available varieties or lines. The preferred method involves (a) identifying several or more varieties or ecotypes adapted to higher latitudes and several or more varieties or ecotypes of the same or closely related species that are adapted to lower latitudes, (b) crossing the varieties within each of the two latitudinal adaptiveness categories, (c)

selecting germplasm from the $F_1$s based on appropriate degrees of divergence in flowering response to photoperiodic treatments as well as timing of megasporogenesis, megagametogenesis, and embryony, and (d) continued selection for each of these traits using conventional breeding regimes (e.g., mass selection, single seed descent). These methods are well known to persons skilled in the art, e.g., Poehlman, Breeding Field Crops (Van Nostrand Reinhold, 1987) (incorporated herein by reference).

Hybridization Processes

The hybridization and amphiploidization processes are facilitated when the selected species are dioecious or self incompatible, have a short juvenile phase, and are amenable to efficient procedures for cytogenetic and embryological analyses of root tips and ovules, respectively. The use of male sterile lines or emasculation procedures are required if the plants are not dioecious or self incompatible. Hybrids are produced between sexual varieties or lines that display appropriate degrees of divergence in photoperiod responses and female developmental schedules. Intraspecific hybrids are made using standard techniques as taught in plant breeding texts, e.g. Poehlman, Breeding Field Crops (1987). The successful production of interspecific or intergeneric hybrids may require hormone treatments to the florets and embryo rescue procedures as taught in recent references involving wide hybridization, e.g. Z. W. Liu et al., Hybrids and Backcross Progenies between Wheat (Triticum aestivum L.) and Apomictic Australian Wheatgrass [Elymus rectisetus (Nees in Lehm.) A. Love & Connor]: Karyotypic and Genomic Analyses, 89 Theor. Appl. Genet. 599–605 (1994) (incorporated herein by reference). Hybrids are verified by their intermediate phenotype.

Amphiploidization Processes

The chromosome numbers of hybrids are doubled using standard colchicine techniques, e.g. J. Torabinejad et al., Morphology and Genome Analyses of Interspecific Hybrids of Elymus scabrus, 29 Genome 150–55 (1987) (incorporated herein by reference). Alternatively, recently developed tissue culture techniques may be used, e.g. O. Leblanc et al., Chromosome Doubling in Tripsacum: the Production of Artificial, Sexual Tetraploid Plants, 114 Plant Breed. 226–30 (1995) (incorporated herein by reference); Salon & Earle, Determination of Mode of Reproduction of Synthetic Tetraploids of Eastern Gamagrass, Agron. Abs. Pg 114 (1994) (incorporated herein by reference); Cohen & Yao, In Vitro Chromosome Doubling of Nine Zantedeschia Cultivars, 47 Plant Cell, Tiss. Org. Cult. 43–49 (1996) (incorporated herein by reference); and Chalak & Legave, Oryzalin Combined with Adventitious Regeneration for an Efficient Chromosome Doubling of Trihaploid Kiwifruit, 16 Plant Cell Rep. 97–100 (1996) (incorporated herein by reference). Partially amphiploid $2n+n$ $B_{III}$ hybrids are often produced in low frequencies (0.5% to 3%) when interspecific $F_1$s are backcrossed, e.g. Z. W. Liu et al., 89 Theor. Appl. Genet. 599–605 (1994), and this frequency may be much higher if tendencies for apomixis (unreduced egg formation) exist in the hybrids as taught in O. Leblanc et al., Reproductive Behavior in Maize-Tripsacum Polyhaploid Plants: Implications for the Transfer of Apomixis into Maize, 87 J. Hered. 108–111 (1996) (incorporated herein by reference). Thus, a preferred method for doubling chromosomes of intraspecific and interspecific hybrids is to use one or more of the colchicine (or other known spindle inhibitor chemical) treatment methods listed above. Likewise, a preferred method for doubling chromosomes of interspecific hybrids involves backcrossing to one of the sexual parents and counting chromosomes in root tips to determine partial amphiploidy (usually triploidy). This is followed by backcrossing to the other parent to obtain a full amphiploid, or to the same parent to obtain a partial amphiploid (three genomes from one parent and one genome from the other). Amphiploidization may precede or follow hybridization.

Procedures for Verifying the Expression of Apomixis

The expression of apomixis in synthetic amphiploids is verified by analyses of megasporogenesis and embryo sac development as taught by J. G. Carman & S. L. Hatch, Aposporous Apomixis in Schizachyrium. Poaceae: Andropogoneae, 22 Crop Sci. 1252–55 (1982) (incorporated herein by reference), for aposporous apomixis and C. F. Crane & J. G. Carman, 74 Amer. J. Bot. 477–96 (1987) (incorporated herein by reference), for diplosporous apomixis. Progeny testing is also useful, as taught in Asker & Jerling.

Some of the features of the present invention may be better appreciated by reference to specific examples. It should be understood that the following examples are illustrative in nature rather than restrictive, and they are meant to demonstrate the basic teachings and concepts of the present invention rather than to limit the invention. It is expected that one of ordinary skill in the art will be able to use the information contained in the examples and elsewhere herein to apply the present invention to situations not specifically described herein.

EXAMPLE 1

Selecting andd Collecting Germplasm—Dicots

It is a feature of the present invention to provide procedures for selecting and collecting the most appropriate lines from within a species or group of closely related species for the purpose of producing apomictic plants. These procedures are believed to mimic and greatly accelerate natural processes that initiate the evolution of apomictic plants from sexual plants, i.e. those natural processes that cause secondary contacts to occur among taxa adapted to greatly divergent climates and photoperiods.

In this example, there is illustrated a preferred procedure for use with plants from the subclass Dicotyledonae. In Example 2 there is illustrated a preferred procedure for use with plants from the subclass Monocotyledonae. The dicotyledonous example involves sexual species from the genus Antennaria (x=14). It is expected that one of ordinary skill in the art could successfully apply these procedures to many species, including various dicotyledonous crops, such as strawberry, Raphanobrassica, potato, cherry, apple, and sugar beet.

The presently preferred procedure of selecting appropriate lines of a given species or closely related group of species begins with (a) identifying geographic distributions from the literature and/or from field studies, and (b) collecting all information concerning the floral biology (photoperiod responses, embryology, etc.) and any specific adaptations of the various ecotypes especially those at the latitudinal extremes. For example, the dicotyledonous genus Antennaria contains 33 sexual species (mostly diploids with some tetraploids) and five large highly polymorphic polyploid agamic (apomictic) complexes. They are dioecious, herbaceous, perennial, and usually stoloniferous.

Apomixis in Antennaria occurs naturally in one of six clades, the Catepes, which contains sexual diploids (2x) and sexual and apomictic polyploids ranging from 4x to 12x. All members of this group are stoloniferous and sexually dimorphic (Bayer, A Phylogenetic Reconstruction of Antennaria Gaertner (Asteraceae: Inuleae), 68 Canad. J. Bot. 1389–97 (1990) (incorporated herein by reference); Bayer, Evolution of Polyploid Agamic Complexes with Examples from Antennaria (Asteraceae), 132 Opera Botanica 53–65 (1996) (incorporated herein by reference)).

Extensive ecological, morphological, and genetic studies indicate that the five polyploid agamic complexes of the Catepes, *A. alpina* (L.) Gaertn., *A. howellii* E. L. Greene, *A. parlinii* Fern., *A. parvifolia* Nutt., and A. rosea, have evolved from among the sexual species. For example, the center of diversity for the *A. rosea* agamic complex is the Rocky Mountains of western North America (near the glacial margins), and its range is from New Mexico and southern California, north to Alaska and the Northwest Territories, and east through Alberta, Saskatchewan, the northern Great Lakes and with disjunct populations in Atlantic Canada. The sexual species believed to have been involved in the initial evolution of *A. rosea* and its subsequent polymorphic expansion include *A. aromatica* Evert, *A. corymbosa* E. Nelson, *A. pulchella* E. Greene, *A. marginata* E. Greene, *A. microphylla* Rydb., *A. racemosa* Hook., *A. rosulata* Rydb. and *A. umbrinella* Rydb. (Bayer, 132 Opera Botanica 53–65 (1996).

The sexual relatives of apomictic *A. rosea* meet the geographic and reproductive criteria listed herein for producing apomictic plants from sexual plants. They have a very broad latitudinal distribution and differences in flowering times, have been noted, e.g. some apomictic forms flower three weeks later than nearby sexual forms (G. L. Stebbins, 94 Bot. Gaz. 322–45 (1932)). Finally, species of Antennaria are easily grown in cultivation, readily hybridized interspecifically (due to lack of internal reproductive isolating mechanisms), and can produce two seed generations per year when vernalized.

Figure 2:
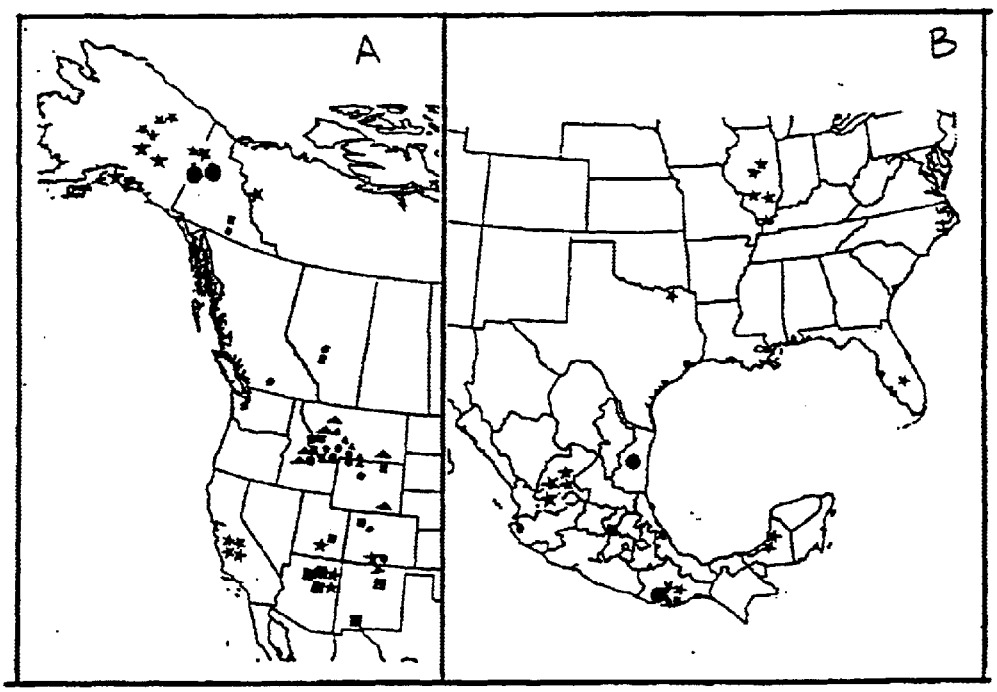
FIGS. 2A–B show examples of the geographic distributions of two plant genera expected to provide adequate divergence in photoperiod responses and reproductive schedules for producing apomictic plants: (A) diploid sexual *Antennaria aromatics* (small triangles in Montana), *A. corymbosa* (two circles by the Idaho Montana border, one circle in Wyoming near the Montana border, one circle in northern Colorado), *A. marginata* (squares in New Mexico and Arizona), A. media/pulchella (stars in California), A. microphylla (one circle in Alberta, one circle near the border of Idaho, Montana, and Wyoming, one circle in north central Wyoming, and one circle in southern Colorado), A. racemosa (one circle in British Columbia, two circles near the Idaho Montana border, and one circle in Montana near the Wyoming border), *A. rosulata* (stars in Utah, Colorado, Arizona, and New Mexico), *A. umbrinella* (large triangles in Idaho, Montana, and Wyoming), *A. friesiana* (small stars in Alaska), *A. densifolia* A. E. Porsild. (circles in the Yukon), *A. monocephala* DC. (large stars in Alaska, the Yukon, and the Northwest Territories), and polyploid apomictic *A. rosea* (small squares); (B) diploid sexual *Tripsacum bravum* Gray (large square in Mexico), *T. dactyloides* (stars in the US), *T. dactyloides* var hispidum (Hitchc.) De Wet and Harlan (large star in Mexico), *T. latifolium* Hitchc. (small square in Mexico), *T. laxum* Nash (large circles in Mexico), *T. maizar* Hernandez and Randolph (triangle in Mexico), *T. manusoroides* de Wet and Harlan (small stars in Mexico near the Gulf of Mexico), *T. pilosum* Scribner and Merrill (small circles in Mexico), and *T. zopilotense* Hernandez and Randolph (small stars in Mexico but not near the Gulf of Mexico). Clones of diploid sexual *T. cundinamarce* de Wet and Timothy, *T. australe* var. australe Cutler and Anderson, and *T. dactyloides* var. meridionale de Wet and Timothy are obtainable from Columbia (near 15 °N lat. 85 °W long.) and are not on the map.

Ramets of Antennaria are collected from sites (FIG. 2A) that provide plant materials representative of extremes and midpoints in latitudinal, ecological, and morphological diversity. Collections are made during the flowering season (June, for lower latitudes; July, for higher latitudes) when species can be confirmed and both staminate and pistillate plants needed for crossing can be identified. The preparation and execution of collection trips involve the study of herbarium voucher specimens and the attainment of appropriate collection permits. Roots of the clones are washed clean and packed in moist sphagnum. Shipments of plants are made by courier every few days during the collection trips to assure survival. The cuttings are potted in standard potting mix and misted during establishment. It will be appreciated that collection and establishment procedures are expected to vary somewhat with each dicotyledonous species.

EXAMPLE 2

Selecting and Collecting Germplasm—Monocots

In this example, there is described an illustrative procedure for selecting and collecting germplasm from plants of the subclass Monocotyledonae. This monocotyledonous example involves sexual species from the genus Tripsacum (x=18). It is expected that one of ordinary skill in the art could successfully apply these procedures to many species, including various monocotyledonous crops, such as sorghum, wheat, barley, rice, and maize.

This example involves the monocotyledonous genus Tripsacum, which is endemic to the new world and is found from 42° N to 24° S latitude (de Wet et al, Systematics of Tripsacum dactyloides (Gramineae), 69 Amer. J. Bot. 1251–57 (1982) (incorporated herein by reference), and from 0 to 2600 m above sea level (Berthaud et al, Tripsacum: Diversity and Conservation, in Taba, Maize Genetic Resources (CIMMYT, 1995) (incorporated herein by reference)) They are monoecious perennials, and the male and female flowers are segregated from each other along the spike. As is typical with many agamic complexes, variation for key characters overlaps among the 16 species, which makes it difficult to classify certain individuals. The *T. dactyloides* agamic complex is the most diverse in the genus. Its range encompasses that of the entire genus, and both sexual diploids and apomictic polyploids are found throughout (de Wet et al., 69 Amer. J. Bot. 1251–57 (1982); Berthaud et al., Tripsacum: Diversity and Conservation, in Taba, Maize Genetic Resources (CIMMYT, 1995)).

Tripsacum diploids are sexual, and all naturally-occurring polyploids studied embryologically are apomictic (Burson et al, Apomixis and Sexuality in Eastern Gamagrass, 30 Crop Sci. 86–89 (1990) (incorporated herein by reference); O. Leblanc et al, Megasporogenesis and Megagametogenesis in Several Tripsacum Species (Poaceae), 82 Amer. J. Bot. 57–63 (1995) (incorporated herein by reference)). This differs from Antennaria, in which sexual autotetraploids occur in nature. Recently, sexual Tripsacum amphiploids have been produced by colchicine doubling of diploids adapted to temperate North American climates (Salon & Earle, Determination of Mode of Reproduction of Synthetic Tetraploids of Eastern Gamagrass, Agron Abs 114 (1994); Salon & Pardee, Registration of SG4X-1 Germplasm of Eastern Gamagrass, 36 Crop Sci. 1426 (1996) (incorporated herein by reference)), and by crossing diploids adapted to tropical Mesoamerican climates followed by colchicine doubling (O. Leblanc et al., Chromosome Doubling in Tripsacum: the Production of Artificial, Sexual Tetraploid Plants, 114 Plant Breed 226–30 (1995) (incorporated herein by reference)).

Figure 3:
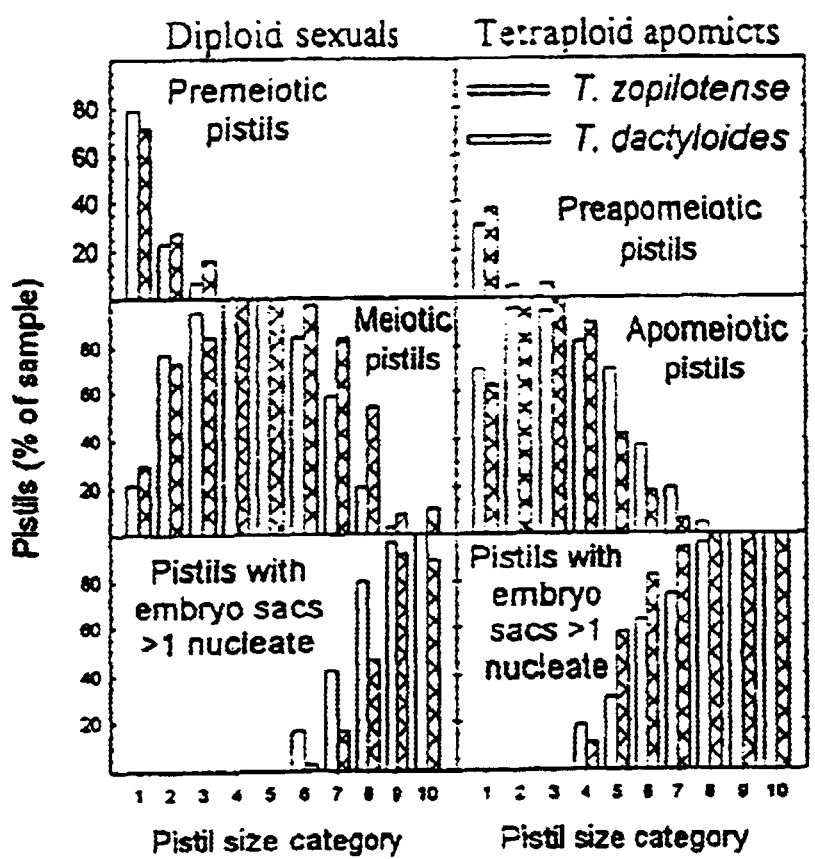
FIG. 3 shows the developmental stage (premeiotic or preapomeiotic, meiotic or apomeiotic, multinucleate embryo sac) of pistils by pistil length for diploid (sexual) and tetraploid (diplosporous) *T. zopilotense* and *T. dactyloides*. Pistil lengths (mm) were <0.50, 0.50–0.75, 0.75–1.00, 1.00–1.25, 1.25–1.50, 1.50–1.75, 1.75–2.00, 2.00–2.25, 2.25–2.50, >2.5 for categories 1–10, respectively. Note that (a) the diploid *T. zopilotense* proceeds through the three stages of female development more rapidly than the diploid *T. dactyloides*, (b) the tetraploids begin apomeiosis sooner than the diploids begin meiosis, and they proceed through the three stages much more rapidly than the diploids (meiosis is skipped in the tetraploids), and (c) the diplosporous *T. dactyloides* proceeds through the three stages more rapidly than the diplosporous *T. zopilotense* (summarized from O. Leblanc & Y. Savidan, Timing of Megasporogenesis in Tripsacum Species (Poaceae) as Related to the Control of Apomixis and Sexuality, 8 Polish Botanical Studies 75–81 (1994) (incorporated herein by reference)).

Sexual Tripsacum diploids (and artificial sexual amphiploids) meet the criteria listed herein for producing apomictic plants from sexual plants. They have a broad geographic distribution with sexual ecotypes distributed throughout (FIG. 2B). The ecotypes are easily grown in cultivation and are readily hybridized. Their ovules are readily examined by interference contrast and fluorescence microscopy, and ecotypic variation in female developmental schedules exists (FIG. 3). Finally, tropical ecotypes remain green year round and flower in the late fall or early winter under short day conditions (10 to 12 h days). In contrast, temperate ecotypes require vernalization followed by long days (14 to 16 h). Tropical and temperate ecotypes will not flower again until specific induction stimuli are repeated.

Ramets of Tripsacum are collected from those sites that will provide plant materials representative of extremes and midpoints in latitudinal, ecological, and morphological diversity, e.g. FIG. 2B. Collections are made during the flowering season (June and July for higher latitudes; September and October for lower latitudes) when species can be confirmed or from living nurseries in the United States and Mexico (CIMMYT). The preparation and execution procedures for collecting Tripsacum germplasm are the same as those presented for Antennaria (Example 1). It will be appreciated that collection and establishment procedures are expected to vary somewhat with each monocotyledonous species.

EXAMPLE 3

Quantifying Effects of Different Photoperiods an Flowering

It is a feature of the present invention to provide procedures for quantifying the effects of different photoperiods on floral development in sexual lines selected as being the most appropriate for producing apomictic plants (Examples 1 and 2). It will be appreciated that many procedures for quantifying such effects have been published in the recent literature, and one skilled in the art may find that procedures other than those described herein are better suited for certain species.

A presently preferred method for quantifying photothermal responses of Antennaria species, which are native to temperate climates (intermediate latitudes) through alpine climates (high latitudes), has been modified from the classic studies on Oxyria digyna (Mooney and Billings, Comparative Physiological Ecology of Arctic and Alpine Populations of Oxyria digyna, 31 Eco. Monog. 1–29 (1961) (incorporated herein by reference)). A set of ecotypes (12 clones of each) is chosen from among the ecotypes identified as being the most appropriate for producing apomictic plants (Example 1), i.e. they represent latitudinal extremes and midpoints. At six weeks after flowering,. four clones of each ecotype are placed in a vernalization growth chamber set for 4° C. (constant) and a 6 h photoperiod (dim light). Four weeks later, four additional clones of each ecotype are added to the vernalization chamber, and this is followed by a third set at eight weeks.

All clones are removed from the vernalization chamber at 12 weeks, which provides three different vernalization exposure groups (4, 8, and 12 weeks). The four clones of each ecotype of each exposure group are randomly assigned to two flower-inducing photoperiods (12 and 16 h) each set for a 22/17° C. day/night temperature regime. Time intervals from the end of vernalization to bud formation, archespore formation, megasporogenesis, megagametogenesis, and flowering (dependent variables) are determined for all clones. Each dependent variable is subjected to analysis of variance and analyzed as a factorial experiment (3X2Xnumber of ecotypes) with replication (repeated with a duplicate set of ecotypes). Cluster analysis (Sneath & Sokal, Numerical Taxonomy: The Principles and Practice of Numerical Classification (1973) (incorporated herein by reference)) is used to group ecotypes exhibiting similar attributes of female development (using phenological, cytological, and photothermal data), and the results are used to predict either asynchronous (apomixis) or synchronous (normal) female development (Table 1) when artificial amphiploids are produced between reproductively divergent ecotypes or reproductively similar ecotypes, respectively.

EXAMPLE 4

Quantifying Effects of Different Photoperiods on Flowering

The presently preferred method for quantifying photothermal responses of Tripsacum species, which are native to tropical climates (low latitudes) through temperate climates (intermediate latitudes), differs from that used for Antennaria (Example 3). Tropical ecotypes often remain green year round and flower in the late fall or early winter under short day conditions (10 to 12 h days). Temperate ecotypes often require vernalization followed by long days (14 to 16 h). Tropical and temperate ecotypes will not flower again until specific induction stimuli are repeated. The presently preferred method takes advantage of these distinctions. A set of ecotypes (16 clones of each) are chosen to represent latitudinal extremes, midpoints, and other significant forms of divergence in female development. Flowering is induced in each ecotype after which noninducive conditions (13 h photoperiod, 30/25 ° C. day/night temperatures) are maintained for a minimum of six weeks after flowering has ceased. Four clones of each ecotype are then placed in a vernalization growth chamber set for 6° C. (constant) and a 13 h photoperiod (dim light). Four weeks later, four additional clones of each ecotype are added to the chamber. This is followed by a third set at eight weeks. The clones in the vernalization chamber are removed at 12 weeks, which provides four different vernalization exposure groups (0, 4, 8, and 12 weeks).

After vernalization, the four clones from each ecotype of each exposure group are randomly assigned to two flower-inducing treatment combinations (two clones in each) defined by two photoperiods (10 and 16 h), each set for a 30/25° C. day/night temperature regime. Time intervals from the end of vernalization to floral bud formation, culm bolting, archespore formation, megasporogenesis, megagametogenesis, and flowering (dependent variables) are determined for all clones. Each dependent variable is subjected to analysis of variance and analyzed as a factorial experiment (4X2Xnumber of ecotypes) with replication (repeated with a duplicate set of ecotyces). Cluster analysis is used to group ecotypes exhibiting similar phenological, cytological, and photothermal characteristics, and the results are used as in the Antennaria example to predict apomictic-like or normal development in artificially-produced interecotypic amphiploids (Table 1).

EXAMPLE 5

Quantifying Divergence in Female Developmental Schedules

It is a feature of the present invention to provide procedures for quantifying divergence among ecotypes in female developmental schedules. A presently preferred method, which is used with both dicotyledonous (e.g. Antennaria) and monocotyledonous (e.g., Tripsacum) plants, is to measure time intervals between floral bud formation, archespore formation, megasporogenesis, megagametogenesis, flowering, fertilization, and early embryo development (2 to 16 cell stage) using a combination of noninvasive measurements and destructive sampling. This information is obtained after the ecotypes chosen in Examples 1 and 2, i.e. those that represent latitudinal and other ecological extremes, have been grown in uniform conditions. Data gathered in Examples 3–5 are obtained simultaneously using the same sets of plants.

Figure 4:
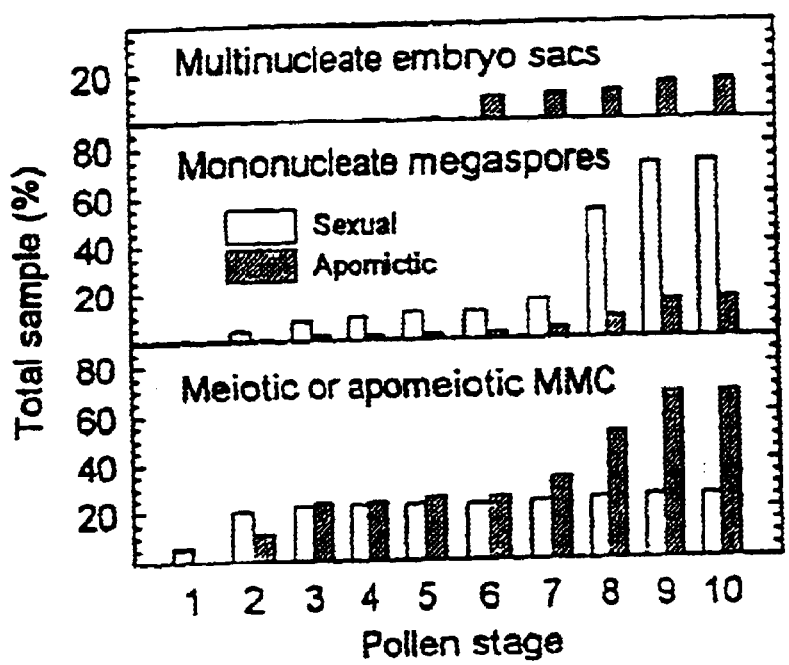
FIG. 4 shows the distribution of 190 pistils from sexual *Elymus scabrus* and 690 pistils from apomictic *Elymus rectisetus* by stage of megasporogenesis (meiotic or apomeiotic MMCs and mononucleate megaspores) or embryo sac development (multinucleate embryo sacs) and corresponding stage of pollen development (1=PMC meiosis II and tetrads; 2=free microspores; 3=pollen grains with incipient germ pore; 4=vacuolate uninucleate pollen prior to formation of Ubisch granules; 5=early Ubisch granule formation to early endothecial wall thickening; 6=endothecial wall thickening; 7=uninucleate pollen without subdivision; 8=pollen with dark-stained single nucleus; 9=pollen with faint-stained single nucleus; 10=binucleate pollen). Bars within stages of female development and above pollen stage designations represent cumulative percentages of the total number of pistils sampled up to the given pollen stage (cumulative across previous pollen stages). Few MMCs were found among sexual pistils after stage three. Thus, bars in this category are nearly equal thereafter. In contrast, bars in the sexual mononucleate megasore category continue to increase in length from stage three through 10, which indicates that most pistils in these stages had advanced beyond the MMC stage. At stage 10, two of three sexual pistils contained multinucleate embryo sacs. Among apomictic pistils, binucleate embryo sacs were first observed at pollen stage three with a large percentage of multinucleate embryo sacs (>2) occurring by pollen stage six (modified from C. F. Crane & J. G. Carman, Mechanisms of Apomixis in *Elymus rectisetus* from Eastern Australia and New Zealand, 74 Amer. J. Bot. 477–96 (1987) (incorporated herein by reference)).
Figure 3:
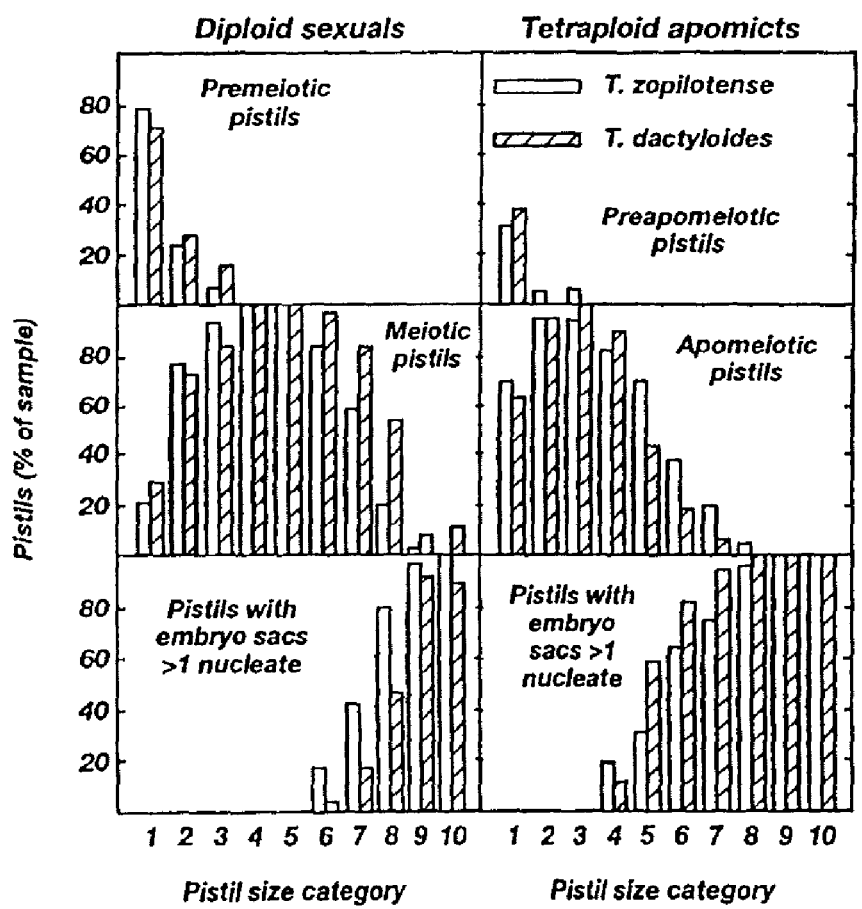
Figure 4:
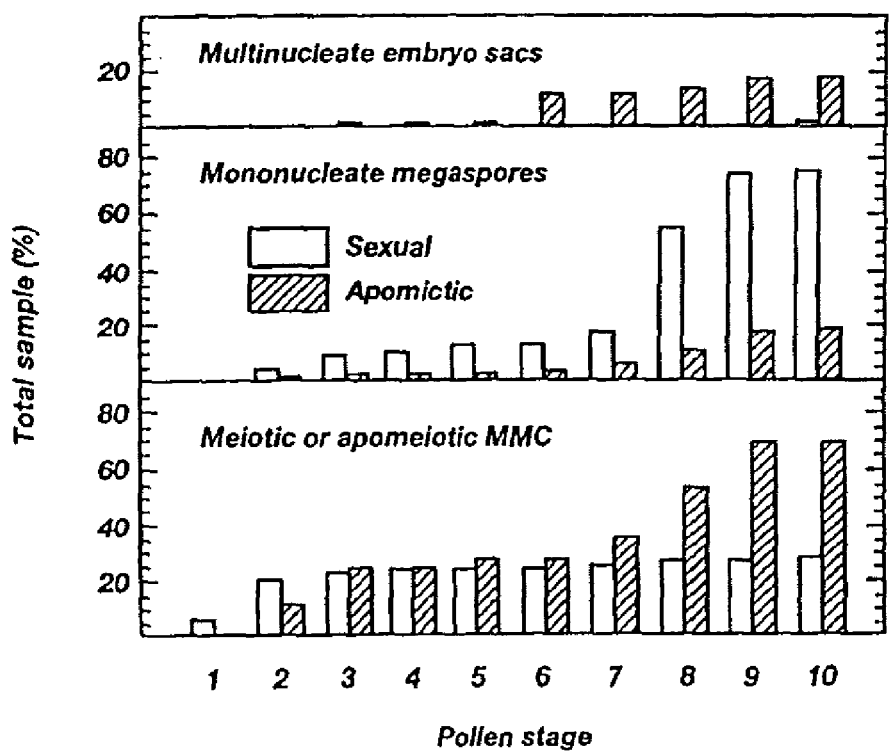

Cytological analyses of the female meiotic prophase, dyad, tetrad, and degenerating megaspore stages and the 1, 2, 4, and 8 nucleate embryo sac stages are conducted, and the following data are obtained for each ovule analyzed: meiotic or embryo sac development stage, pistil length and width, inner and outer integument lengths, and meiocyte or embryo sac length and width. Pistils for cytological analysis are killed, fixed, cleared, observed, and measured as in C. F. Crane & J. G. Carman (74 Amer. J. Bot. 477–96 (1987)), J. G. Carman et al., Comparative Histology of Cell Walls During Meiotic and Apomeiotic Megasporogenesis in Two Hexaploid Australian Elymus Species, 31 Crop Sci. 1527–32 (1991) (incorporated herein by reference); M. D. Peel et al., 37 Crop Sci. 724–32 (1997) (incorporated herein by reference); and M. D. Peel et al., Meiotic Anomalies in Hybrids Between Wheat and Apomictic Elymus rectisetus (Nees in Lehm.) A. Love & Connor, 37 Crop Sci. 717–23, (1997) (incorporated herein by reference)). Developmental stage data are graphed against (a) pistil and integument lengths and widths (raw data) and (b) the lengths and widths of these structures represented as percentages of their mature lengths and widths (measured at stigma exsertion). The likeness of ecotypes with respect to female developmental schedules is tested by analysis of variance, and diagrams patterned after FIGS. 3 and 4 and Table 2 are produced and used with the cluster analyses of Examples 3 and 4 to predict apomictic-like or normal development in artificially-produced interecotypic amphiploids (Table 1).

Table 2 shows relationships between pistil length and developmental stage of sexual (diploid) and diplosporous (polyploid) Tripsacum pistils as determined by analyses of cleared ovules using Nomarski interference contrast microscopy.

TABLE 2

Numbers or pistils analyzed by pistil length (mm)[†]

| Stage[‡] | 0.75–1.00 | 1.00–1.25 | 1.25–1.50 | 1.50–1.75 | 1.75–2.00 | 2.00–2.25 | 2.25–2.50 | >2.50 |
|---|---|---|---|---|---|---|---|---|
| Sexual | | | | | | | | |
| 4-nucleate ES | | | | | | | | 1 |
| 2-nucleate ES | | | | | | | 3 | 7 |
| Degen-tetrad | | | 3 | 9 | 18 | 10 | 6 | 4 |
| Tetrad | | | 19 | 17 | 7 | 3 | 1 | |
| Dyad | | 6 | 13 | 4 | | | | |
| MMC | 6 | 3 | | | | | | |
| Diplasporous | | | | | | | | |
| 8-nucleate ES | | | | | 1 | 4 | 3 | 2 |
| 4-nucleate ES | | | | 7 | 18 | 14 | 7 | 5 |
| 2-nucleate ES | | | 16 | 21 | 11 | 3 | | |
| Metaphase | | 7 | | | | | | |
| large MMC | | 29 | 21 | 5 | | | | |
| MMC | 17 | | | | | | | |

[†]pistils were pooled across species and ploidy levels (see Table 1).
[‡]ES: embryo sac; Degen tetrad: tetrad in which the three megaspores in the micropylar region were degenerating; Metaphase: MMC in apomeiotic metaphase (from M.D. Peel et al., 37 Crop Sci. 724–32 (1997).

EXAMPLE 6
Obtaining Greater Divergence in Female Developmental Schedules

It will be appreciated that sufficient divergence in (a) flowering responses to different photoperiods and (b) female developmental schedules will not be expressed among extant ecotypes of many cosmopolitan species even though sufficient genetic variability to establish such divergence by breeding may exist within their primary gene pools, i.e. within each cosmopolitan species as a whole. It is a feature of the present invention to provide breeding guidelines for increasing such divergence. As noted by D. Wilson, Breeding for Morphological and Physiological Traits, in K. J. Frey (ed), Plant Breeding II (Iowa State University Press, 1981) (incorporated herein by reference), many morphological and physiological traits, including flowering response to day length, are quantitatively inherited, which means they are influenced by many genes. Thus, much progress towards increasing the day length in which plants respond by flowering can be expected by intercrossing lines already showing some tendencies for this trait and selecting from among the progeny those lines that show greater tendencies. Much progress can be expected by repeating this process over several generations. In a similar manner, significant decreases in the day length in which plants respond by flowering can be expected by intercrossing lines already showing this tendency and following a similar regime of repeated selection and breeding. The traits for which it is presently preferred that divergence be maximized by such breeding schemes include (a) flowering responses to different photoperiods, i.e. producing long and short day ecotypes, and (b) accelerated and delayed initiations of archespore formation, meiosis, embryo sac development, etc, relative to the development of nongametophytic ovule and ovary tissues.

It will be appreciated that sufficient divergence in floral development will generally not be expressed among extant ecotypes of non-cosmopolitan species even though sufficient genetic variability to establish such divergence by breeding may exist within their secondary and tertiary gene pools, i.e. within the same genus, tribe, or family. It is contemplated that wide hybridization and even genetic engineering may in the future be used to incorporate into targeted species genes for (a) appropriate flowering responses and (b) appropriate divergence in female developmental schedules.

EXAMPLE 7
Making Apomictic Plants from Sexual Lines Divergent in Floral Development The techniques in Examples 1 through 6 are used as guidelines to obtain three or more lines of the same species (or closely related group of species) distinctly adapted to long days (14 to 20 h) and generally an early archespore development/early meiosis/early gametophyte development relative to the development of nongametophytic ovule and ovary tissues (nucellus, integuments, pericarp, etc). The same techniques are used as guidelines to obtain three or more lines of the same species (or group of species) distinctly adapted to short days (10 to 12 h) and generally a late archespore development/late meiosis/late gametophyte development relative to the development of nongametophytic ovule and ovary tissues. The several lines of each category (long-day plants and short-day plants, etc) are selected such that they form a continuum with regard to the day length in which flowering responses are induced, e.g. somewhat long, long, and very long and somewhat short, short, and very short. The lines are selected such that the initiation of embryo sac formation (degenerating megaspore stage) in one set of lines (usually the long-day-adapted lines) occurs at about the same time as female meiotic prophase through metaphase is occurring in the other set of lines relative to the development of the nongametophytic tissues of the ovule and ovary.

Amphiploids are then produced using the standard procedures described above (colchicine induction or through repeated s production of $B_{III}$ hybrids) or other appropriate procedures. Standard hybridization procedures are used for producing hybrids among Tripsacum species. For Antennaria, pistillate plants are isolated by placing pollination bags (made from laboratory tissues, e.g. KIMWIPES) over the entire capitulescence. Pollination is accomplished by rubbing receptive pistillate inflorescences together with staminate heads at anthesis. Unpollinated control capitulescences are used to verify absence of apomixis of each parent clone. This is especially important with tetraploid clones in which either amphimictic or apomictic reproduction occurs. The pollination bags hold the fruits as they mature, and no embryo rescue is required.

At least three of the nine possible combinations of parents (one from each adaptation group) are made into amphiploids initially: the somewhat early line with the somewhat late line, the early line with the late line, and the very early line with the very late line. These are checked for the expression of apomixis as described above. Additional amphiploids from the nine possibilities are made if apomixis is not expressed. It will be appreciated that the genetic background in which the lines are derived may influence the expression of apomixis. Thus, the selection or production of additional lines incorporating different genetic backgrounds may occasionally be necessary.

EXAMPLE 8
Producing Apomictic Monocotyledonous and Dicotyledonous Plants

The techniques set forth in Examples 1 through 7. are used to obtain apomictic plants from sexual dicotyledonous or sexual monocotyledonous plants.

The highly efficient production of apomictic plants from sexual plants of many angiospermous genera is obtained by following the practices taught herein. Apomixis has been occasionally observed in man-made hybrids and amphiploids involving both monocotyledonous and dicotyledonous plants (Linnean; Asker & Jerling). The reasons offered for these infrequent occurrences are speculative and fail to teach the duplicate gene asynchrony concept. Furthermore, they are not supported by phylogenetic, genetic, physiological, or developmental studies. The common explanation given for these reports is that specific apomixis gene(s) are present in the parents but are suppressed by diploidy or an inappropriate genetic background (Asker & Jerling). This is reasonable for examples involving agamic complexes. For example, G. L. Stebbins, Cytology of Antennaria. I. Normal Species, 94 Bot. Gaz. 134–51 (1932), documented aposporous embryo sac formation in a hybrid between sexual Antennaria neglecta and sexual Antennaria plantaginifolia. Likewise, Nordberg, Embryological Studies in the Sanguisorba minor Complex (Rosaceae), 120 Botaniska Notiser 109–19 (1967) (incorporated herein by reference). produced all combinations of hybrids between two sexual tetraploid and one sexual octaploid Sanguisorba spp, and all of the resulting tetraploid and hexaploid $F_1$s produced aposporous embryo sacs in which the unreduced eggs formed embryos either parthenogenetically or after fertilization. Furthermore, A. Jankun & M. Kovanda, Apomixis at the Diploid Level in Sorbus eximia (Embryological Studies in Sorbus 3), 60 Preslia, Praha, 193–213 (1988) (incorporated herein by reference), documented fully functional, high frequency apospory and diplospory in both diploid and tetraploid Sorbus eximia, which is a geographically-restricted hybridogenous species derived from Sorbus aria and Sorbus torminalis, both of which are sexual diploids. These three examples involve agamic complexes in which apomixis gene(s) could have remained unexpressed in the sexual diploid progenitors. In contrast, other examples exist that involve taxa unrelated to agamic complexes.

Low frequency apomixis (parthenogenesis from unreduced eggs) was reported in three trispecific hybrids in the Triticeae (A. Mujeeb-Kazi, Apomictic Progeny Derived from Intergeneric Hordeum-Tritium Hybrids, 72 J. Hered. 284–85 (1981) (incorporated herein by reference) A. Mujeeb-Kazi, Apomixis in Trigeneric Hybrids of Triticum aestivum/Leyus racemosusl/Thinopyrum elongatum, 61 Cytologia 15–18 (1996) (incorporated herein by reference); R. von Bothmer et al, Complex Interspecific Hybridization in Barley (Hordeum vulgare L.) and the Possible Occurrence of Apomixis, 76 Theor. Appl. Genet. 681–90 (1988) (incorporated herein by reference), and none involved Elymus rectisetus, the only apomict in the Triticeae, or even other Elymus sp.

A much higher frequency of apomixis was observed in hybrids between sexual amphiploids of Raphanus sativus and Brassica oleraceae. From 36 to 70% of ovules in six of 10 hybrids produced contained from 1.6 to 2.9 aposporic embryo sacs (S. Ellerström & L. Zagorcheva, Sterility and Apomictic Embryo Sac Formation in Raphanobrassica, 87 Hereditas 107 (1977) (incorporated herein by reference), and a maternal descendant of an aposporic Raphanobrassica was documented (S. Ellerström, Apomictic Progeny from Raphanobrassica, 99 Hereditas 315 (1983) (incorporated herein by reference). Apospory is not expressed elsewhere in the parental species, genera, family, or entire Brassicales (Linnean), which strongly suggests that apospory did not in this case surface as a result of a gradual accumulation of developmentally-suppressed apomixis genes. To this effect, S. Ellerström & L. Zagorcheva, 87 Hereditas 107 (1977), stated:

"In our opinion it seems therefore, more justified to conclude that the formation of aposporic embryo-sacs in Raphanobrassica is caused by physiological disturbances, as a result of defective cooperation between the two parent genomes in the hybrid, rather than to assume the presence of specific genes governing the formation of such embryo-sacs."

Sven Ellerström died shortly after this research was conducted, and follow-up studies were not performed. Neither S. Ellerström & L. Zagorcheva, 87 Hereditas 107 (1977) (incorporated herein by reference), nor S. Ellerström, 99 Hereditas 315 (1983) (incorporated herein by reference), speculated as to the nature or cause of the intergenomic physiological disturbances responsible for apospory in Raphanobrassica beyond the wide hybridization explanation offered by Ernst. Nor did they identify how such disturbances might explain the evidence for relatively simple Mendelian inheritance in many apomicts and the fact that some apomicts appear to have arisen from autopolyploidy. These deficiencies were resolved in a study of the phylogeny and genomic composition of reproductive anomalies in angiosperms (Linnean) wherein asynchronous expression of duplicate-genes was identified. This concept explains essentially all major inconsistencies in the apomixis literature and is supported by numerous phylogenetic, genetic, genomic, and physiological studies (Linnean; M. D. Peel et al., 37 Crop Sci. 724–32 (1997); M. D. Peel et al., Crop Sci 37, 717–23 (1997)).

It will be appreciated that the present invention may be embodied in other specific forms without departing from its spirit or essential characteristics, which reside in the discovery that apomixis is caused by asynchronous expression of duplicate genes for female developmental pathways. The described steps and materials are to be considered in all respects only as illustrative and not restrictive, and the scope of the invention is indicated by the appended claims rather than be the foregoing description. All changes which come within the meaning and range of equivalency of the claims are to be embraced within their scope.

I claim:

1. A method for obtaining apomictic plants from sexual plants, wherein the method comprises:

(a) obtaining two diploid delineated sexual plants from an angiospermous plant species, genus, or family, wherein the diploid delineated sexual plants express differences in their flowering responses to various photoperiods and differ such that initiation of embryo sac formation in one diploid delineated sexual plant occurs at about the same time as or before meiosis in the other diploid delineated sexual plant relative to the developmental maturity of the nongametophytic ovule and ovary tissues;

(b) hybridizing said two diploid delineated sexual plants, (c) recovering seed therefrom, (d) sowing said seed, and (e) selecting diploid hybrid plants that are apomictic.

2. The method of claim 1 wherein the two sets of diploid delineated sexual lines are short-day plants.

3. The method of claim 1 wherein each of the two sets of diploid delineated sexual lines is of a different response type selected from the group consisting of short-day plants, long-day plants, dual-day-length plants, intermediate-day-length plants ambiphotoperiodic plants, and day-neutral plants.

4. The method of claim 1 wherein the nongametophytic ovule and ovary tissues comprise at least one member of the group consisting of nucellus, integument, pericarp, hypanthium, and pistil wall.

5. The method of claim 1 wherein said hybrid lines display a reproductive anomaly selected from the group consisting of apospory, diplospory, and polyembryony.

6. The method of claim 1 wherein the differences in flowering responses are measured in days to flowering.

7. The method of claim 1 wherein the two sets of diploid delineated sexual lines are long-day plants.

8. The method of claim 1 wherein the two sets of diploid delineated sexual lines are dual-day-length plants.

9. The method of claim 1 wherein the two sets of diploid delineated sexual lines are intermediate-day-length plants.

10. The method of claim 1 wherein the two sets of diploid delineated sexual lines are ambiphotoperiodic plants.

11. The method of claim 1 wherein the two sets of diploid delineated sexual lines are day-neutral plants.

12. A method for obtaining apomictic plants from sexual plants, wherein the method comprises:
    (a) screening plants within an angiospermous plant species, genus, or family for differences in flowering responses to various photoperiods and for differences among the plants in their times of initiation of embryo sac formation and times of meiosis relative to the developmental maturity of the nongametophytic ovule and ovary tissues;
    (b) selecting two plants that differ in their flowering responses to various photoperiods and that differ such that initiation of embryo sac formation in one plant occurs at about the same time as or before meiosis in the other plant relative to the developmental maturity of the nongametophytic ovule and ovary tissues;
    (c) producing diploid hybrid plants that express apomixis by hybridizing said two plants,
    (d) recovering hybrid seed therefrom,
    (e) sowing said hybrid seed, and
    (f) selecting diploid hybrid plants that are apomictic.

13. A method for obtaining polyembryonic plants from sexual aposporic, diplosporic, monocotyledonous or dicotyledonous plants, wherein the method comprises:
    (a) screening plants within an angiospermous plant species, genus, or family for differences in days to flowering or photoperiod required to induce flowering,
    (b) and for differences in their start times and durations of female or seed developmental stages, wherein the stages are selected from the group consisting of archespore formation, megasporogenesis, megagametogenesis, and early embryony, and wherein the differences are relative to the the developmental maturity of the nongametophytic ovule and ovary tissues, wherein the tissues are selected from the group consisting of nucellus, integument, pericarp, hypanthium, and pistil wall;
    (b) selecting two plants that differ
        (i) in their days to flowering or photoperiod required to induce flowering, and
        (ii) such that initiation of embryo sac formation in one plant occurs at about the same time as or before meiosis in the other plant relative to the developmental maturity of the nongametophytic ovule and ovary tissues; and
    (c) producing progeny plants that are apomictic by sexually crossing the two plants.

14. A method for producing apomictic plants from sexual plants, wherein the method comprises:
    (a) obtaining two sexual diploid plants of the same angiospermous species, genus, or family, wherein the female reproductive phenotypes of the plants differ such that under similar environmental conditions initiation of embryo sac formation in one sexual diploid plant occurs at about the same time as or before meiosis in the other sexual diploid plant relative to the developmental maturity of the nongametophytic ovule and ovary tissues; and
    (b) hybridizing the two sexual diploid plants,
    (c) obtaining diploid progeny therefrom, and
    (d) selecting apomictic plants from among said diploid progeny.

15. A method for obtaining apomictic plants from sexual plants, wherein the method comprises:
    (a) obtaining two diploid delineated sexual plants from an angiospermous plant species, genus, or family selected from families that exhibit apomixis in nature, wherein said plants differ in days to flowering or photoperiod required to induce flowering and differ such that initiation of embryo sac formation in one plant occurs at about the same time as or before meiosis in the other plant relative to the developmental maturity of the nongametophytic ovule and ovary tissue; and
    (b) hybridizing said plants,
    (c) recovering seed therefrom,
    (d) sowing said seed, and
    (e) selecting diploid hybrid plants that are apomictic.

16. A method for obtaining apomictic plants from sexual plants comprising:
    (a) obtaining two diploid delineated sexual plants from an angiospermous plant species or genus selected from the grass family, wherein said plants differ in days to flowering or photoperiod required to induce flowering and differ such that initiation of embryo sac formation in one plant occurs at about the same time as or before meiosis in the other plant relative to the developmental maturity of the nongametophytic ovule and ovary tissue; and
    (b) hybridizing said plants,
    (c) recovering seed therefrom,
    (d) sowing said seed, and
    (e) selecting diploid hybrid plants that are apomictic.

17. A method for obtaining apomictic plants from sexual plants comprising:
    (a) obtaining two diploid sexual plants from an angiospermous plant species or genus selected from the Asteraceae family, wherein said plants differ in days to flowering or photoperiod required to induce flowering and differ such that initiation of embryo sac formation in one plant occurs at about the same time as or before meiosis in the other plant relative to the developmental maturity of the nongametophytic ovule and ovary tissue; and
    (b) hybridizing said plants,
    (c) recovering seed therefrom,
    (d) sowing said seed, and
    (e) selecting diploid hybrid plants that are apomictic.

* * * * *

UNITED STATES PATENT AND TRADEMARK OFFICE
CERTIFICATE OF CORRECTION

PATENT NO. : 6,750,376 B1
DATED : June 15, 2004
INVENTOR(S) : Carman

It is certified that error appears in the above-identified patent and that said Letters Patent is hereby corrected as shown below:

Title page,
Item [56], References Cited, OTHER PUBLICATIONS,
"Dung et al." reference, after "its association with a gene" delete "expresses" and insert -- expressed --.
"Eshed et al." reference, change "Less-than-epistatic" to -- Less-than-additive-epistatic --.
"Holm et al." reference, after "crossing experiments" delete "withdiploid" and insert -- with diploid --.
"Kenny et al." reference, delete "et al.".
"Purnhauser et al." reference, after "A method" delete "fro" and insert -- for --.
"Asker and Jerling" reference, (first listing) after "apomixis in Plants, p. 81-107, 241-283, delete "1982" and insert -- 1992 --.
"Hussey et al." reference, after "sexual embryo sacs in facultative", delete "apomietic" and insert -- apomictic --.
"Carman, John G.," reference, after "*Asynchronous Expression of Duplicate Genes in*", delete "*Agniosperms*" and insert -- *Angiosperms* --.
"Carman, J.G." reference, (second listing) before "Sep. 25-27, College Station, Texas (1995), delete "Apomi" and insert -- Apomix --.
"Carman, J.G." reference, (third listing) after "*Comparative Histology of Cell Walls During Meiotic and Apomeiotic*", delete "*Megasporoge*" and insert -- *Megasporogenesis* --.
"Carman, J.G." reference, (fourth listing) after "Crop Science", delete "2" and insert -- 22 --
"Crane, C.F. et al." reference, after "*Eastern Australia and New*", delete "*Zeala*" and insert -- *Zealand* --.
"Ellerstrom S. et al." reference, after "Hereditas 87:" delete "10" and insert -- 107 --.
"Knox, R.B. et al." reference, after "*Apomixis in a Grass of the Andropogoneae*,", delete "Botanisk" and insert -- Botaniska --.

Drawings,
Delete Drawing FIGS. 1-4 and substitute therefor Drawing FIGS. 1-4 on attached sheets.

UNITED STATES PATENT AND TRADEMARK OFFICE
CERTIFICATE OF CORRECTION

PATENT NO. : 6,750,376 B1
DATED : June 15, 2004
INVENTOR(S) : Carman

It is certified that error appears in the above-identified patent and that said Letters Patent is hereby corrected as shown below:

Column 27,
Line 43, delete "(b)".
Line 48, delete the second occurrence of "the".

Signed and Sealed this

Twenty-third Day of November, 2004

JON W. DUDAS
*Director of the United States Patent and Trademark Office*

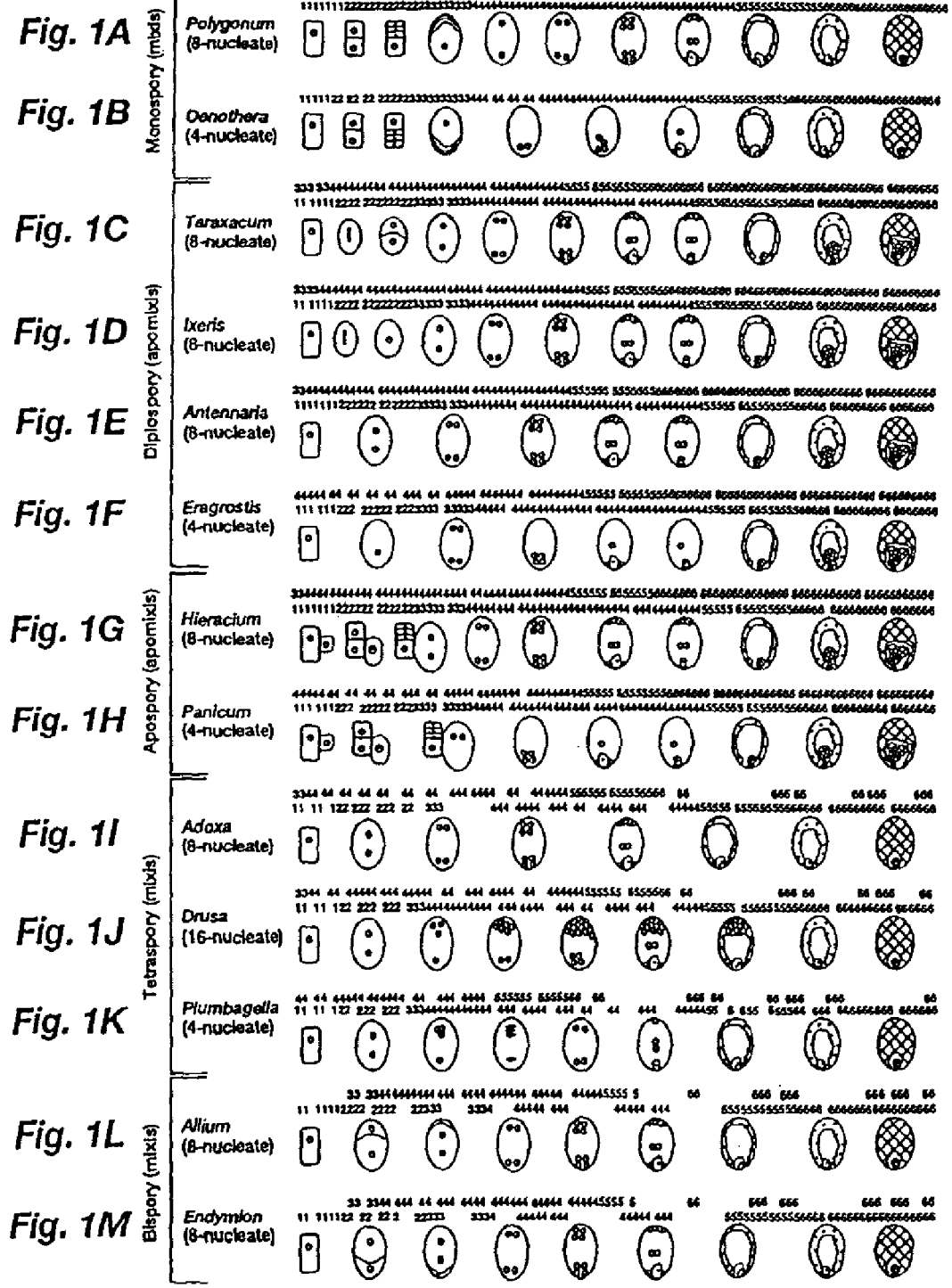
Fig. 1A Polygonum (8-nucleate)
Fig. 1B Oenothera (4-nucleate)
Fig. 1C Taraxacum (8-nucleate)
Fig. 1D Ixeris (8-nucleate)
Fig. 1E Antennaria (8-nucleate)
Fig. 1F Eragrostis (4-nucleate)
Fig. 1G Hieracium (8-nucleate)
Fig. 1H Panicum (4-nucleate)
Fig. 1I Adoxa (8-nucleate)
Fig. 1J Drusa (16-nucleate)
Fig. 1K Plumbagella (4-nucleate)
Fig. 1L Allium (8-nucleate)
Fig. 1M Endymion (8-nucleate)

*Fig. 2A*  *Fig. 2B*